US012793880B2

(12) United States Patent
Tsourkan et al.

(10) Patent No.: US 12,793,880 B2
(45) Date of Patent: Nov. 10, 2026

(54) CORE ASSEMBLY AND CORE MOUNT FOR USE IN X-RAY GENERATION UNIT OF A MEDICAL IMAGING DEVICE

(71) Applicant: GE Precision Healthcare LLC, Waukesha, WI (US)

(72) Inventors: Evguen Tsourkan, Meudon (FR); Baptiste Salvi, Saint-Cloud (FR); Nicolas Levilly, Magny les Hameaux (FR); Yuan Fang, Puteaux (FR)

(73) Assignee: GE Precision Healthcare LLC, Waukesha, WI (US)

( * ) Notice: Subject to any disclaimer, the term of this patent is extended or adjusted under 35 U.S.C. 154(b) by 154 days.

(21) Appl. No.: 18/963,073

(22) Filed: Nov. 27, 2024

(65) Prior Publication Data

US 2026/0148887 A1 May 28, 2026

(51) Int. Cl.

| | |
|---|---|
| ***H01F 27/06*** | (2006.01) |
| ***A61B 6/40*** | (2024.01) |
| ***H01F 27/24*** | (2006.01) |
| ***H05G 2/00*** | (2006.01) |

(52) U.S. Cl.

CPC ............... *H01F 27/06* (2013.01); *A61B 6/40* (2013.01); *H01F 27/24* (2013.01); *H05G 2/00* (2013.01)

(58) Field of Classification Search

CPC ........... H01F 27/06; H01F 27/24; A61B 6/40; H05G 2/00

See application file for complete search history.

(56) References Cited

U.S. PATENT DOCUMENTS

2016/0217901 A1 * 7/2016 Klinkowstein ..... H01F 27/2823

* cited by examiner

*Primary Examiner* — Jurie Yun

(74) *Attorney, Agent, or Firm* — Foley & Lardner LLP

(57) ABSTRACT

An assembly is configured for use in an X-ray generation unit of a medical imaging device. The assembly includes a core assembly, a core mount, and one or more ties configured to couple the core assembly to the core mount. The core assembly includes a magnetic core, a plurality of insulated cables, a plurality of standoffs, and a core mount. Each of the standoffs is configured to couple to an end of each of the insulated cables. The core mount is configured to receive the core assembly. The core mount includes a longitudinal section extending along a first plane, a lateral section extending from the longitudinal section along a second plane, and a plurality of receptacles extending from the lateral section. Each of the receptacles is substantially perpendicular to the second plane and includes a receptacle aperture configured to receive one of the standoffs.

20 Claims, 21 Drawing Sheets

CORE ASSEMBLY AND CORE MOUNT FOR USE IN X-RAY GENERATION UNIT OF A MEDICAL IMAGING DEVICE

FIELD

Embodiments of the subject matter disclosed herein relate to medical imaging devices, and more particularly, to providing a core assembly and a core mount for use in an X-ray generation unit of a medical imaging device.

BACKGROUND

Medical imaging devices can create detailed images of a patient's internal structures. Some medical imaging devices contain components such as high-power magnetic cores, which are used to generate and stabilize strong and uniform magnetic fields for producing diagnostic images. These images are subsequently analyzed by a clinician to observe a condition or to identify any abnormalities.

SUMMARY

An embodiment relates to an assembly configured for use in an X-ray generation unit of a medical imaging device. The assembly includes a core assembly, a core mount, and one or more ties configured to couple the core assembly to the core mount. The core assembly includes a magnetic core, a plurality of insulated cables configured to electrically couple to the magnetic core, and a plurality of standoffs, each of the standoffs configured to couple to an end of each of the insulated cables. The core mount is configured to receive the core assembly. The core mount includes a longitudinal section extending along a first plane, a lateral section extending from the longitudinal section along a second plane, a plurality of receptacles. The plurality of receptacles extend from the lateral section. Each of the receptacles is substantially perpendicular to the second plane. Each of the receptacles comprises a receptacle aperture configured to receive one of the standoffs.

Another embodiment relates to an assembly for use in an X-ray generation unit of a medical imaging device. The assembly includes a core assembly and a core mount. The core assembly includes a magnetic core, a plurality of insulated cables configured to electrically couple to the magnetic core, and a plurality of standoffs. Each of the standoffs is configured to couple to an end of each of the insulated cables. The core mount is configured to receive the core assembly. The core mount includes a longitudinal section extending along a first plane, a lateral section extending from the longitudinal section along a second plane, and a plurality of receptacles extending from the lateral section. Each of the receptacles is substantially perpendicular to the second plane. Each of the receptacles forms a polygon cross-section. Each of the receptacles includes a receptacle aperture configured to receive one of the standoffs. Each of the receptacles forms a plurality of sides. Each of the sides includes a protrusion extending from a first end of the receptacle to a location closer to the second end of the receptacle than the first end of the receptacle. The protrusion is configured to prevent the standoff from rotating.

Another embodiment relates to an assembly for use in an X-ray generation unit of a medical imaging device. The assembly includes a core assembly and a core mount. The core assembly includes a magnetic core, a plurality of insulated cables configured to electrically couple to the magnetic core, and a plurality of standoffs. Each of the standoffs is configured to couple to an end of each of the insulated cables. The core mount is configured to receive the core assembly. The core mount includes a longitudinal section extending along a first plane. The longitudinal section includes a first planar portion extending along the first plane, a second planar portion offset from the first plane, and a third planar portion extending along the first plane. The core mount includes a lateral section extending from the longitudinal section along a second plane and a plurality of receptacles extending from the lateral section. Each of the receptacles includes a receptacle aperture configured to receive one of the standoffs. The second planar portion extends between the first planar portion and the third planar portion.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
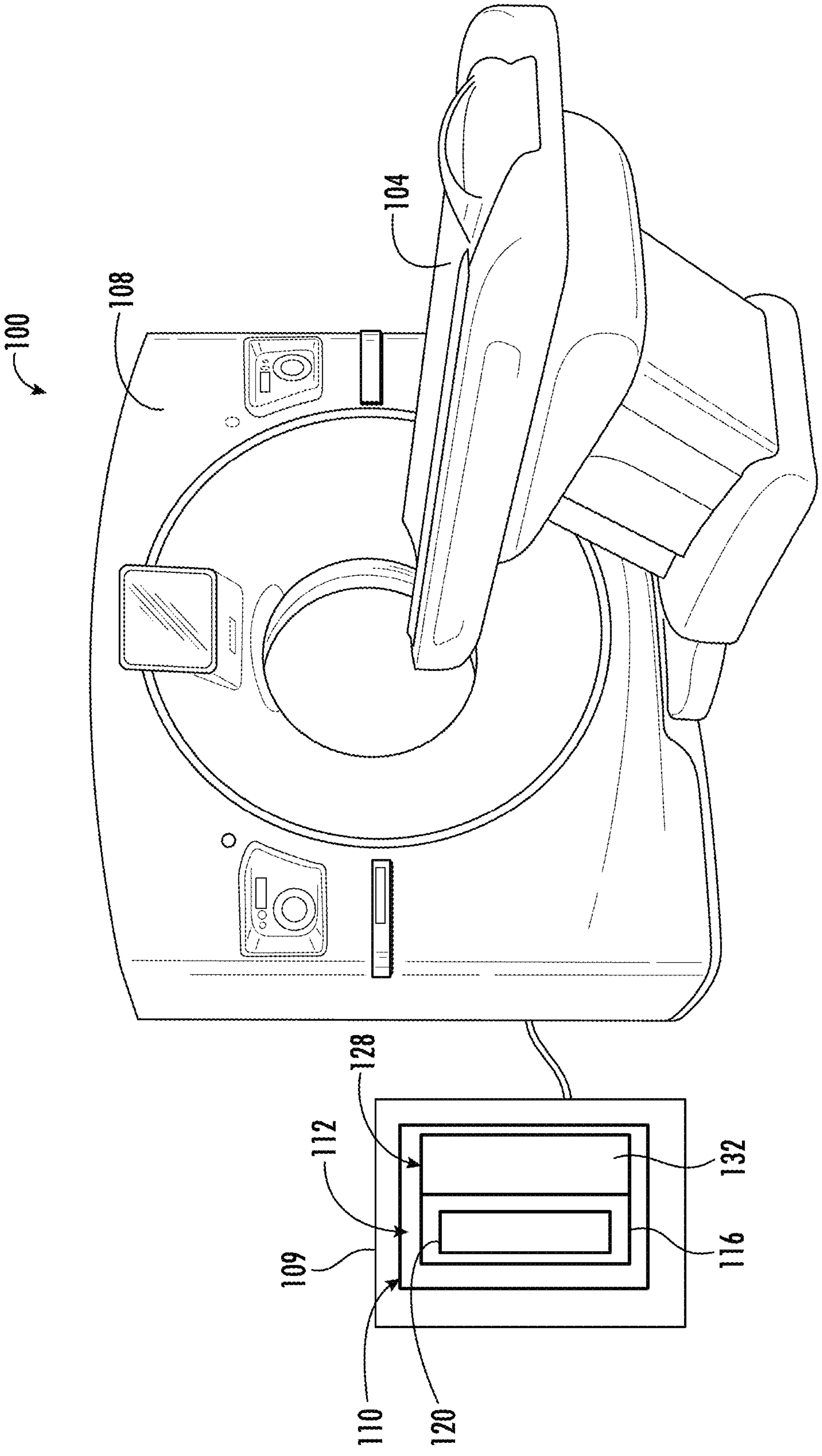
FIG. 1 is a perspective view of a medical imaging system including an X-ray generation unit, according to an example embodiment.

Referring generally to the figures, an assembly including an X-ray generation system for use in an imaging system is disclosed. The X-ray generation system includes an assembly, and the assembly includes a core mount and a core assembly. The core assembly is configured to be received within the core mount, and the assembly is configured to be received within the X-ray generation system. The core assembly includes a high-power magnetic core configured to enhance the strength and uniformity of magnetic fields generated by the imaging system. The assembly disclosed herein integrates high-power magnetics with mechanical parts to create the assembly. Currently, a lack of standardization regarding the mounting of high-power magnetic cores within the imaging system results in inefficient installation times, overheated components, expensive manufacturing costs, and non-compact systems.

The imaging system industry faces constraints due to busy schedules of technicians, limited appointment times, high patient volumes, scheduling conflicts, and so on. These constraints place additional pressure on assembly professionals to assemble the imaging system as quickly as possible so the imaging system can be received by a hospital, be operational, and perform imaging procedures on patients. These constraints increase the desirability of the imaging system to be capable of being easy to assemble. This also increases the desirability of the imaging system to include components that provide features to indicate the components are assembled correctly and increases the desirability of efficient and fast assembly workflows. For example, the additional pressure faced by assembly professionals may lead to rushed imaging system assembly, which in turn, can be detrimental to the performance of an imaging system, and in turn, be detrimental to examinations and to a patient's health.

In addition to the inconsistencies and pressures associated with assembling imaging systems a described above, assembly technicians may receive inadequate training and/or possess inadequate experience in assembling imaging devices. Such inadequacies among assembly technicians may result in errors, delays, and further inconsistencies within imaging device. Therefore, components of imaging devices that provide locating features and precises fits are desirable in the imaging domain. During shipment of the imaging system, parts may also become dislocated or misaligned within the system. Therefore, components that contain additional constraints to prevent dislocation during shipment may be desirable.

Additional imaging systems may provide space constraints both within the imaging system or during shipping. The space constraints may lead to performance issues. Additionally, fulfilling the space constraints may present issues with respect to the cooling of components within the imaging system while maintaining performance.

Unlike existing technology, the systems and methods disclosed herein provide an assembly including a core assembly and a core mount that reduces manufacturing time and cost, reduces assembly time and cost, and results in high reliability during assembly due to locating features. An assembly professional can easily determine if the part is assembled correctly, since the locating features provide locational constraints for components of the imaging device. Additionally, the systems and methods disclosed herein are designed to be as small as possible to fit space constraints in a limited volume. Therefore, the assembly provides a high performance within a minimized volume. The system is also easily shipped without dislocating components and optimizes mechanical holding of the high-power magnetic core with air flow and cooling of components. Furthermore, eliminating the inconsistencies within assembling imaging systems minimizes errors in assembling the imaging system.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring to FIG. 1, a perspective view of an imaging device 100 is shown. The imaging device 100 may be used in a medical environment (e.g., hospitals, clinics, etc.), for example, by a technician or other clinician certified to collect imaging data from a patient. The medical imaging device 100 can be any medical imaging device employing X-rays. For example, the medical imaging device 100 can be a magnetic resonance (MR) imaging device, a computed tomography (CT) imaging device, an X-ray imaging device, an interventional imaging guided system, among others.

An example of a procedure performed using the imaging device 100 may be a CT scan of the abdomen and pelvis. A patient lies on a table (e.g., table 104, as described below) that slides into the imaging device 100 and a health care professional administers a contrast material either orally or through an IV line. A gantry (e.g., a gantry within the outer housing 108, etc.) of the imaging device 100 rotates around the patient, capturing multiple X-ray images (e.g., using the X-ray generation unit 110 of the imaging device 100, as described herein) from different angles. The collected data is then processed to create cross-section images of the abdomen and pelvis. Another example of a procedure performed using the imaging device 100 may be a chest X-ray. Chest X-rays are typically performed to assess the lungs and the heart of a patient by collecting and processing radiographic images (e.g., using the imaging device 100, as described herein) of the patient's chest. A tube generates X-rays and a detector captures the images, which are then processed electronically or chemically to create visuals of the chest structure.

As shown in FIG. 1, the medical imaging system 100 includes a table 104 (e.g., bed, patient table, etc.) and an outer housing 108 (e.g., a gantry, enclosure, external casing, frame, etc.). The outer housing 108 is configured to receive the table 104. The outer housing 108 includes a circular frame that encircles the table 104. In some imaging systems, the imaging system includes a bore having internal components that rotate around the table 104 during scanning. The outer housing 108 also shields a patient and operator against radiation.

Figure 2:
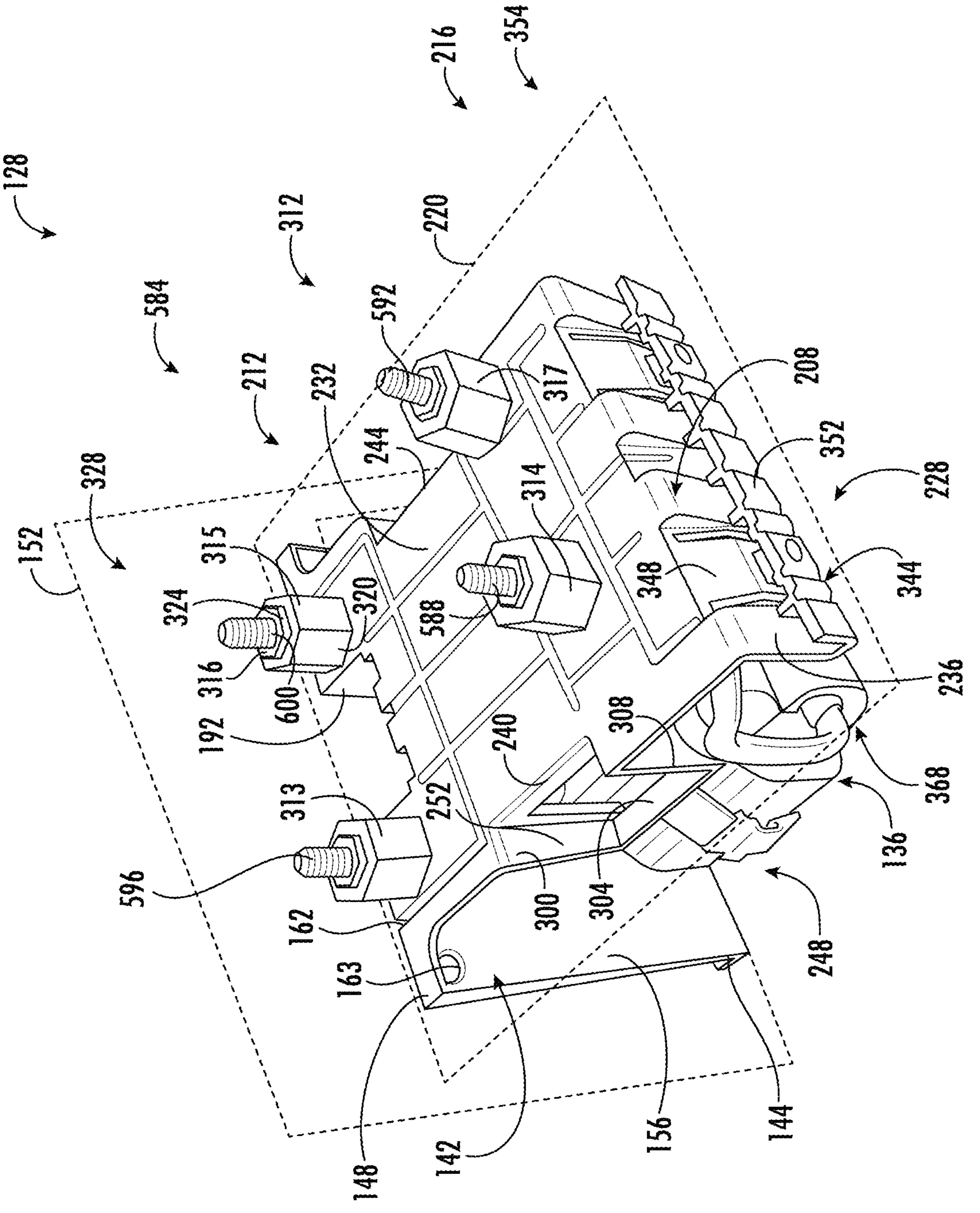
FIG. 2 is a perspective view of an assembly including a core assembly and a core mount used in the X-ray generation unit of FIG. 1, according to an example embodiment.
Figure 3:
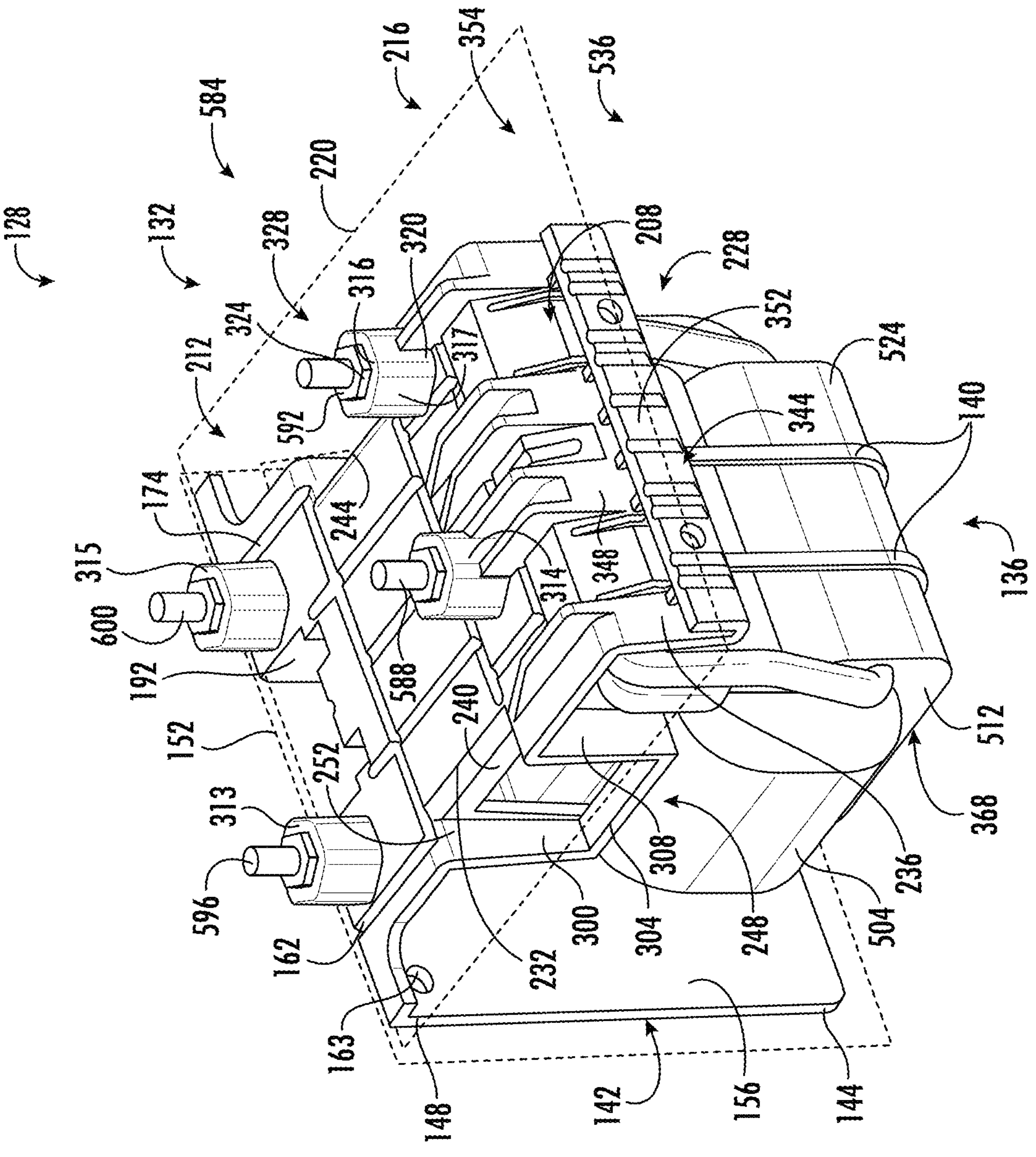
FIG. 3 is a perspective view of an assembly including a core assembly and a core mount used in the X-ray generation unit of FIG. 1, according to an example embodiment.
Figure 4:
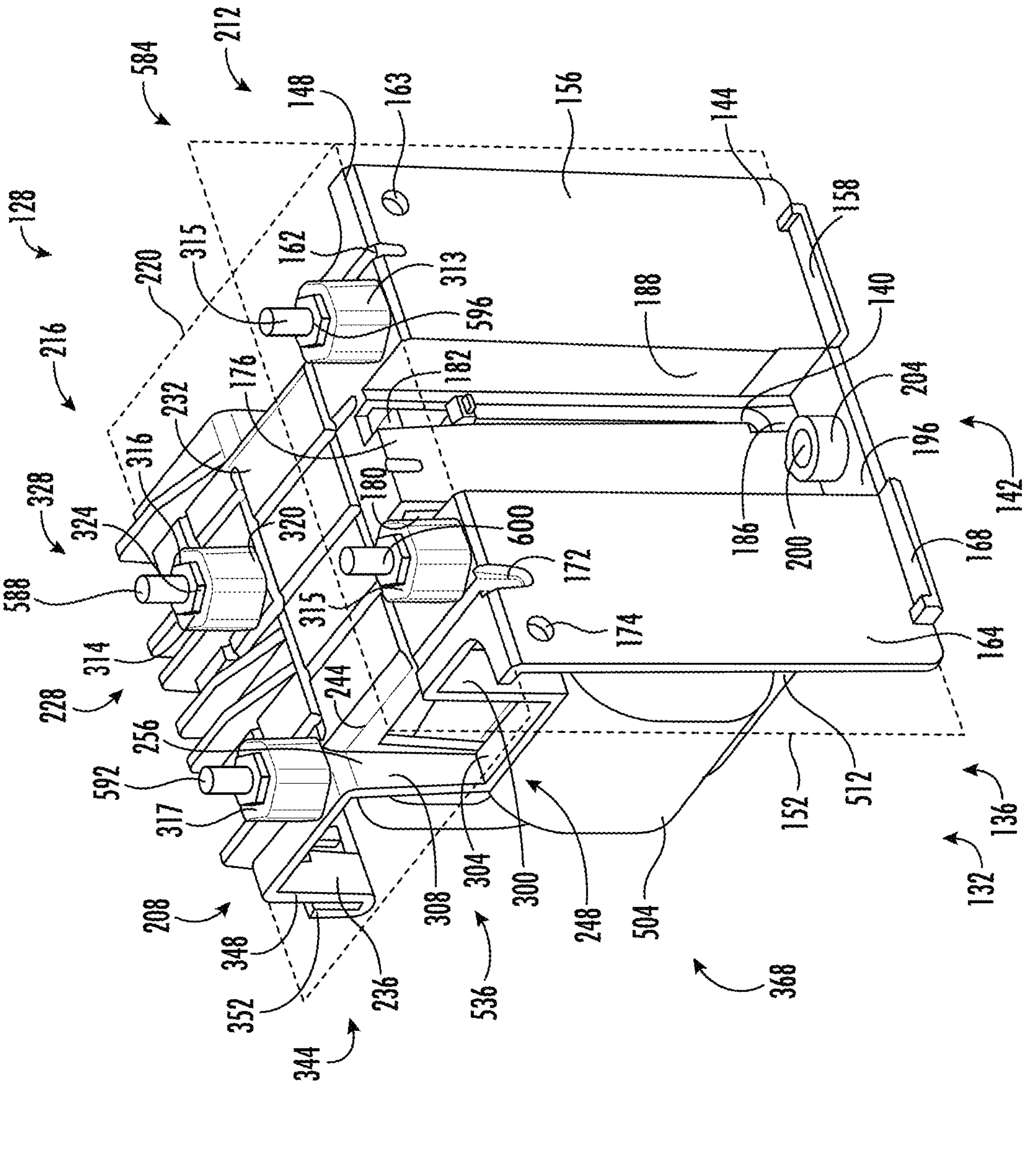
FIG. 4 is another perspective view of the assembly of FIG. 3, according to an example embodiment.
Figure 5:
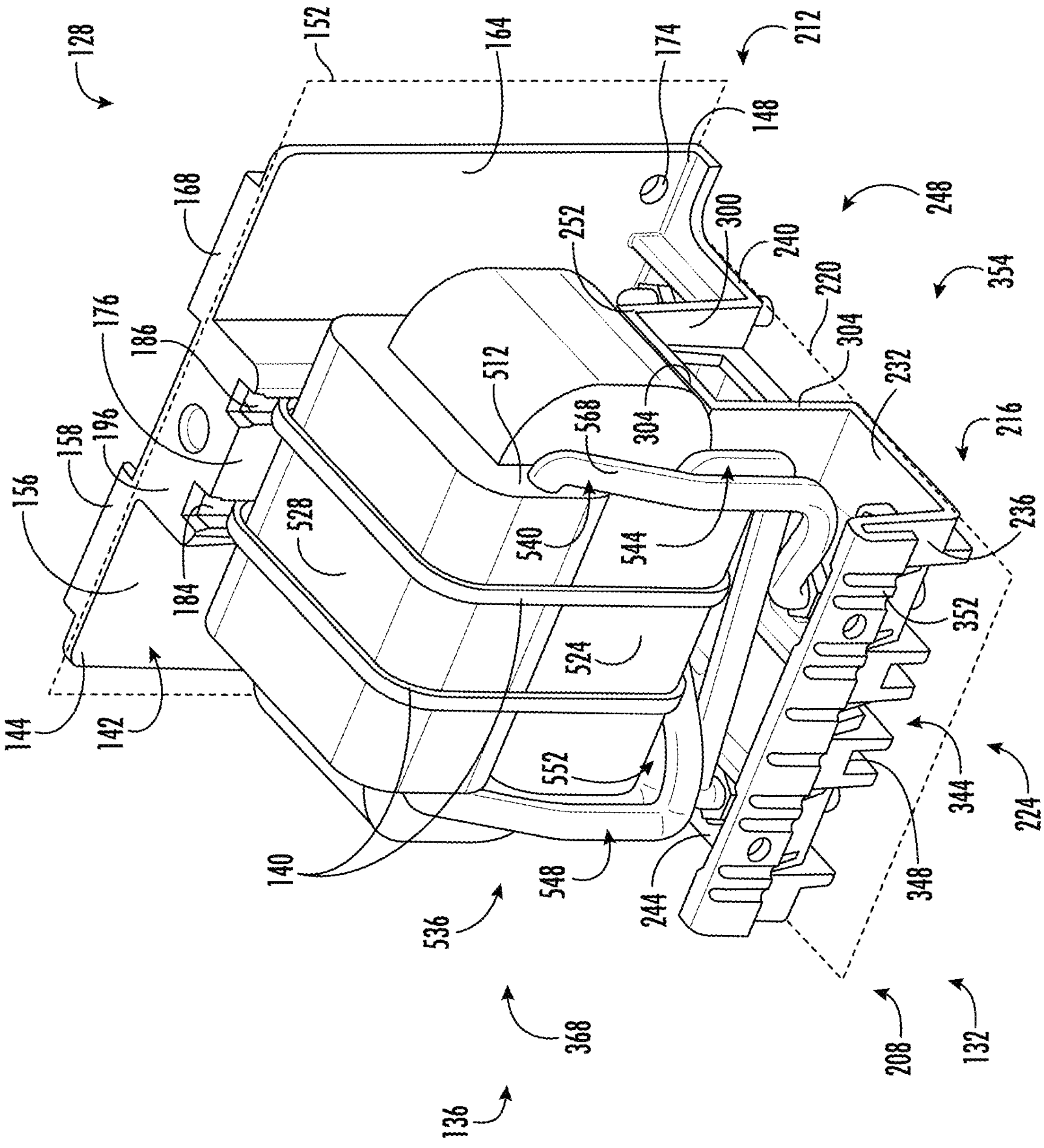
FIG. 5 is another perspective view of the assembly of FIG. 3, according to an example embodiment.
Figure 6:
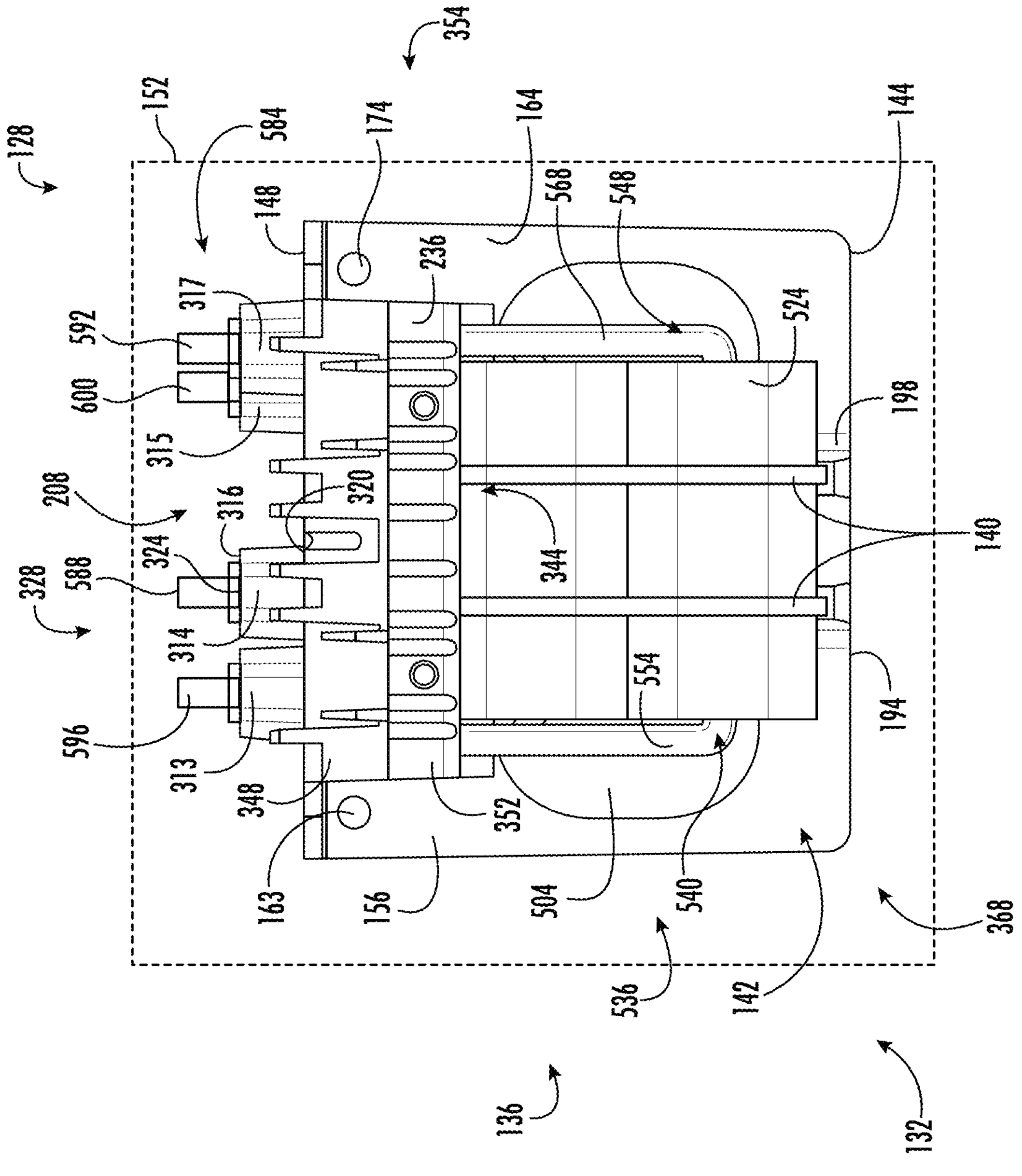
FIG. 6 is a front view of the assembly of FIG. 3, according to an example embodiment.
Figure 7:
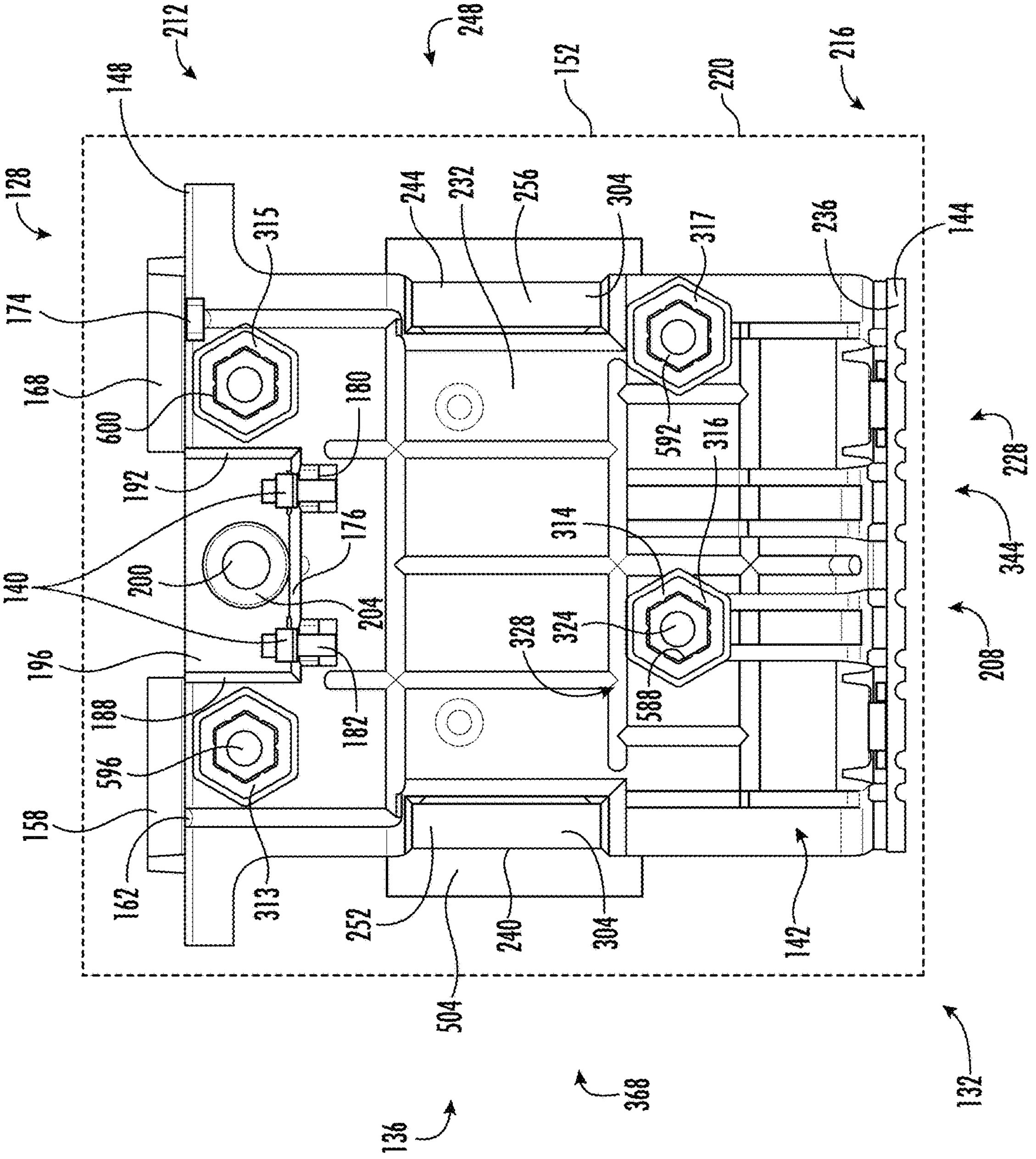
FIG. 7 is a top view of the assembly of FIG. 3, according to an example embodiment.

The medical imaging system 100 can include a cabinet 109 (e.g., power distribution unit (PDU), electrical cabinet, etc.). The cabinet 109 is electrically coupled to the internal components of the outer housing 108. The cabinet 109 includes an X-ray generation unit 110 (e.g., X-ray source etc.). The X-ray generation unit 110 includes an inner housing 112 (e.g., internal casing, frame, enclosure, etc.). The inner housing 112 includes a heat sink 116 (e.g., heat exchanger, etc.), a circuit board 120 (e.g., a printed circuit board, etc.), a fan 124 (e.g., air flow device, propeller, blower, etc.), and an assembly 128 (e.g., magnetic module, module, etc.). The heat sink 116 is configured to absorb and dissipate heat to maintain an optimal operating temperature for the X-ray generation unit 110. In the illustrated embodiment, the heat sink 116 is 5 kg. In other embodiments the heat sink 116 may be more or less than 5 kg (e.g., 10 kg, 2 kg, etc.). The circuit board 120 is configured to process data that may be used to generate images and to control various functions within the imaging device 100. The fan 124 is configured to manage airflow and increase heat dissipation to provide effective cooling and prevent overheating. The spatial relationships of components within the inner housing 112 are discussed in further detail below. While FIG. 2 depicts the example cabinet 109 as positioned adjacent to the outer housing 108, in other examples, the cabinet 109 and/or the components of the cabinet 109 are positioned within the outer housing 108.

Figure 8:
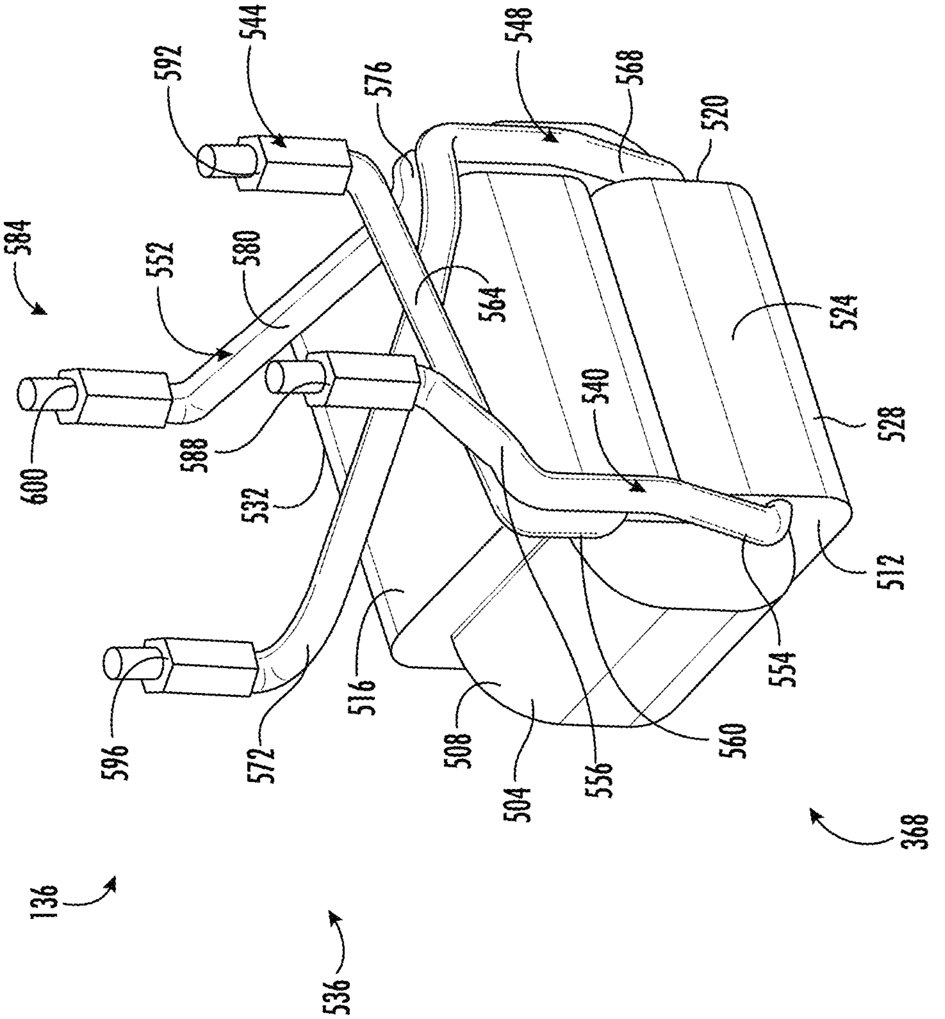
FIG. 8 is a perspective view of the core assembly of FIG. 3, according to an example embodiment.
Figure 9:
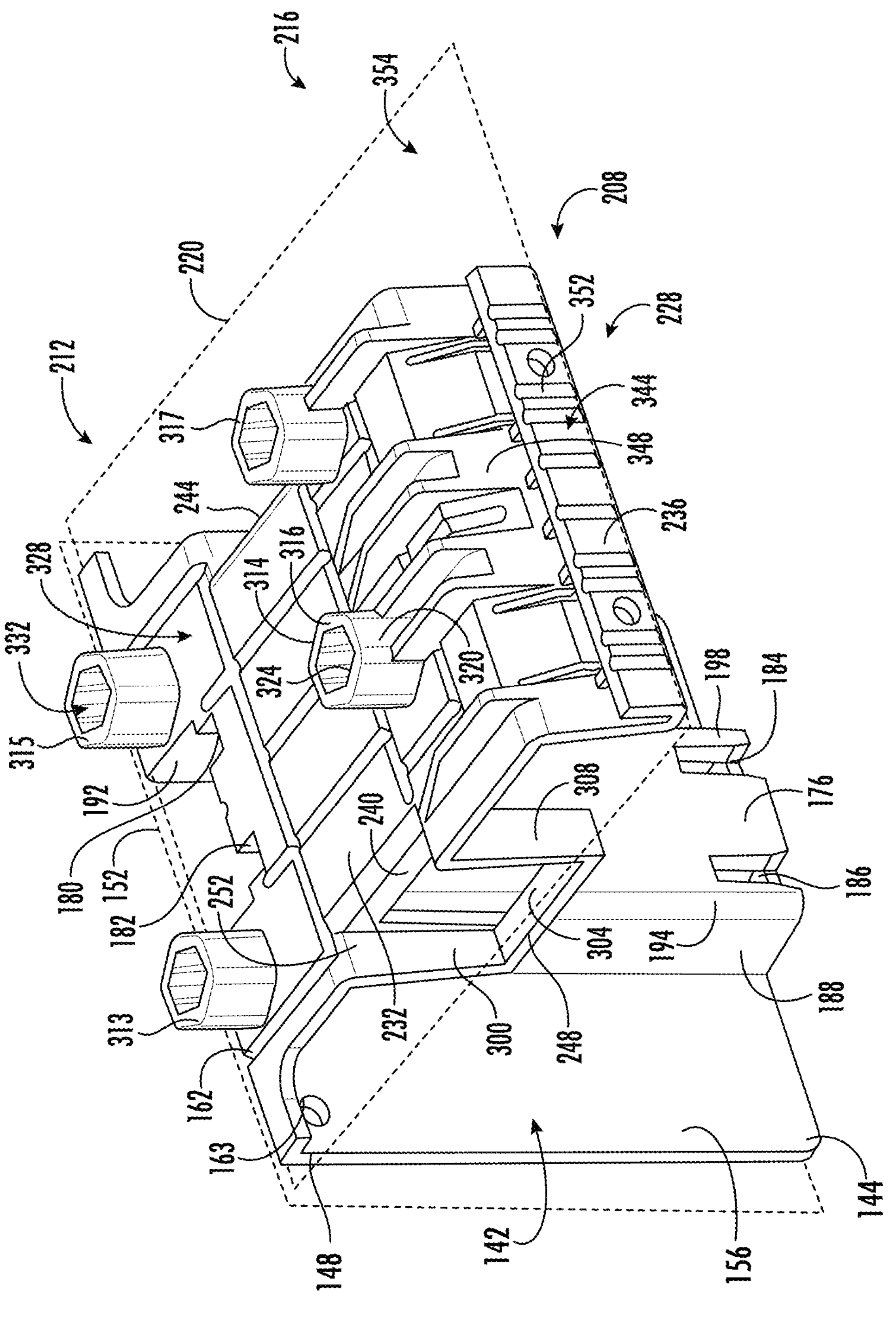
FIG. 9 is a perspective view of the core mount of FIG. 3, according to an example embodiment.
Figure 10:
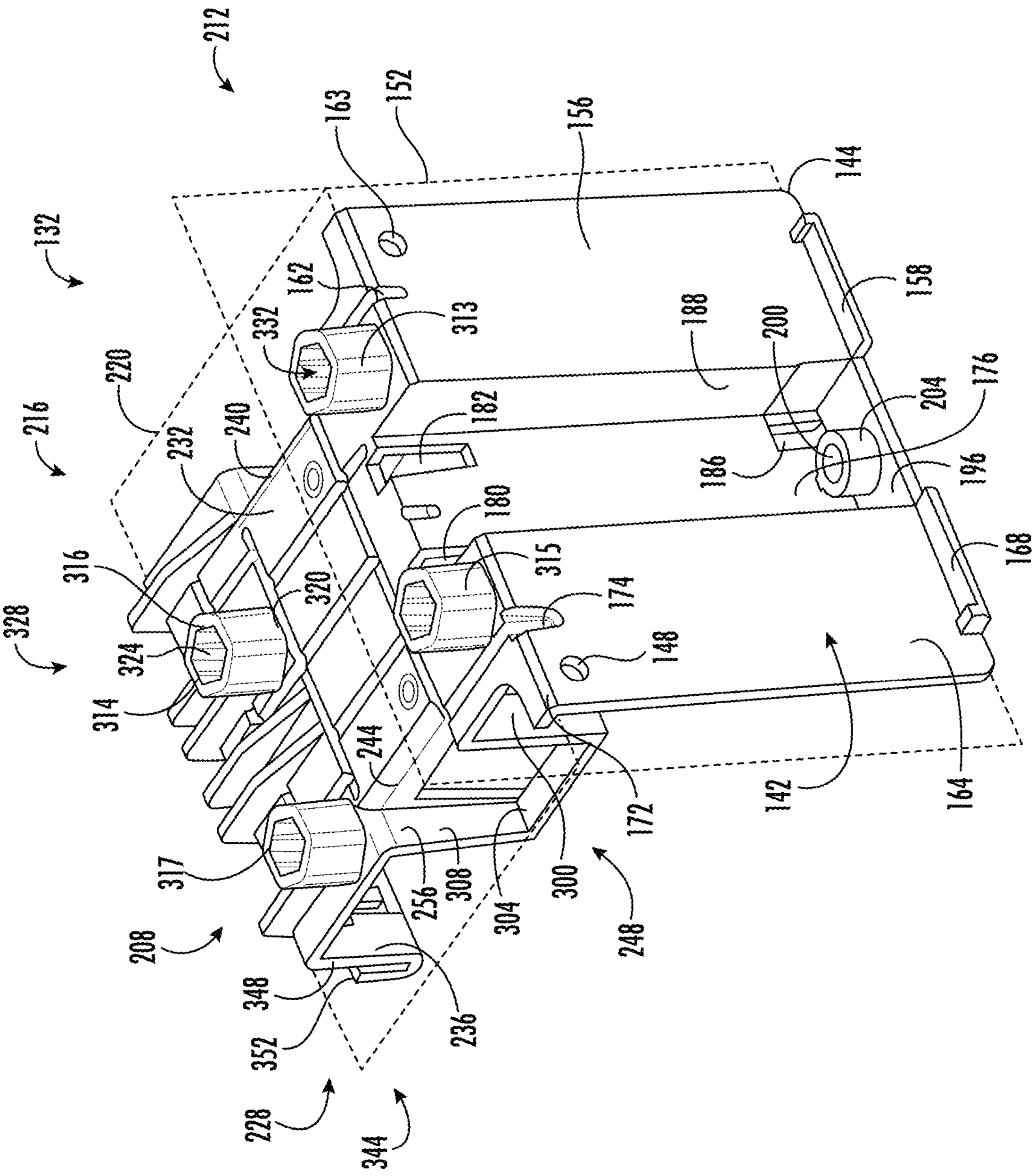
FIG. 10 is another perspective view of the core mount of FIG. 3, according to an example embodiment.
Figure 11:
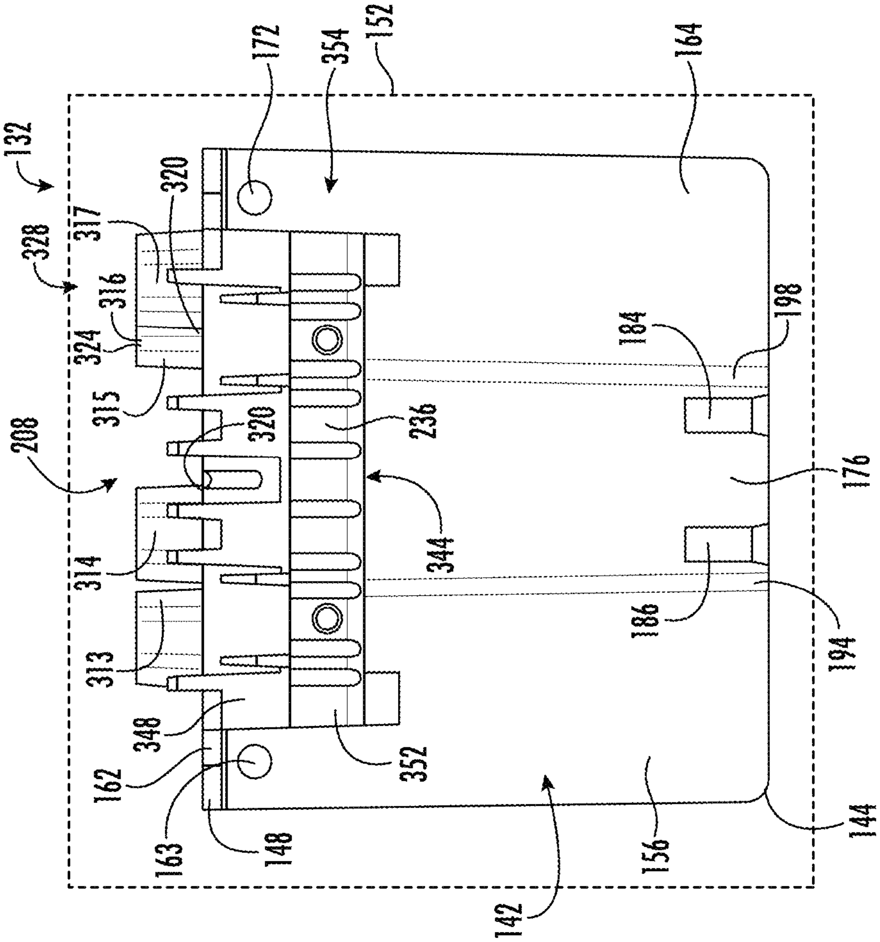
FIG. 11 is a front view of the core mount of FIG. 3, according to an example embodiment.
Figure 12:
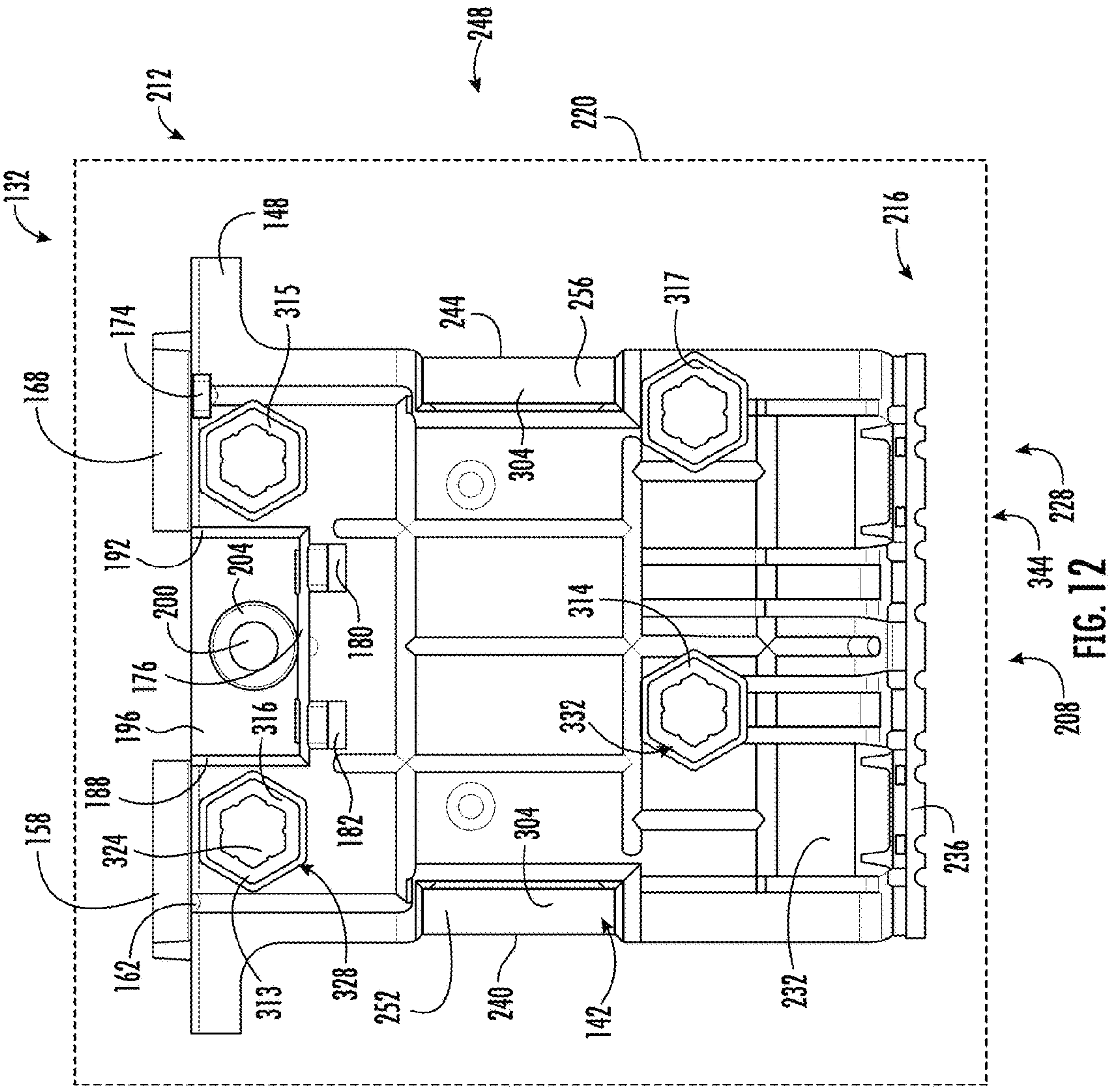
FIG. 12 is a top view of the core mount of FIG. 3, according to an example embodiment.

FIGS. 2-7 show the assembly 128, according to example embodiments. In general, the assembly 128 is configured to step up voltage for X-ray production. The assembly 128 includes a core mount 132 (e.g., mounting bracket, base, holder, etc.), also shown in FIGS. 9-13, a core assembly 136 (e.g., core unit, core module, etc.), also shown in FIG. 8, and ties 140 (e.g., fasteners, link, strap, etc.), as shown in FIGS. 2-7. The core assembly 136 is coupled to the core mount 132 with the ties 140. The ties 140 are configured to withstand high temperatures (e.g., to meet UL94 standards, polycarbonate, polypropylene, thermoplastic elastomers, etc.).

Referring now to FIGS. 2-7 and FIGS. 10-13 the core mount 132 forms a substantially L-shaped side profile. The core mount 132 may be manufactured using Selective Laser Sintering (SLS), as in FIG. 2, or injection molded, as in FIGS. 3-7 and FIGS. 9-13. In other embodiments, the core mount 132 may be manufactured by alternative methods (e.g., vacuum formed, 3-D printed, compression molded, etc.). The core mount 132 is a material configured to withstand high temperatures (e.g., to meet UL94 standards, polycarbonate, polypropylene, thermoplastic elastomers, etc.).

Figure 18:
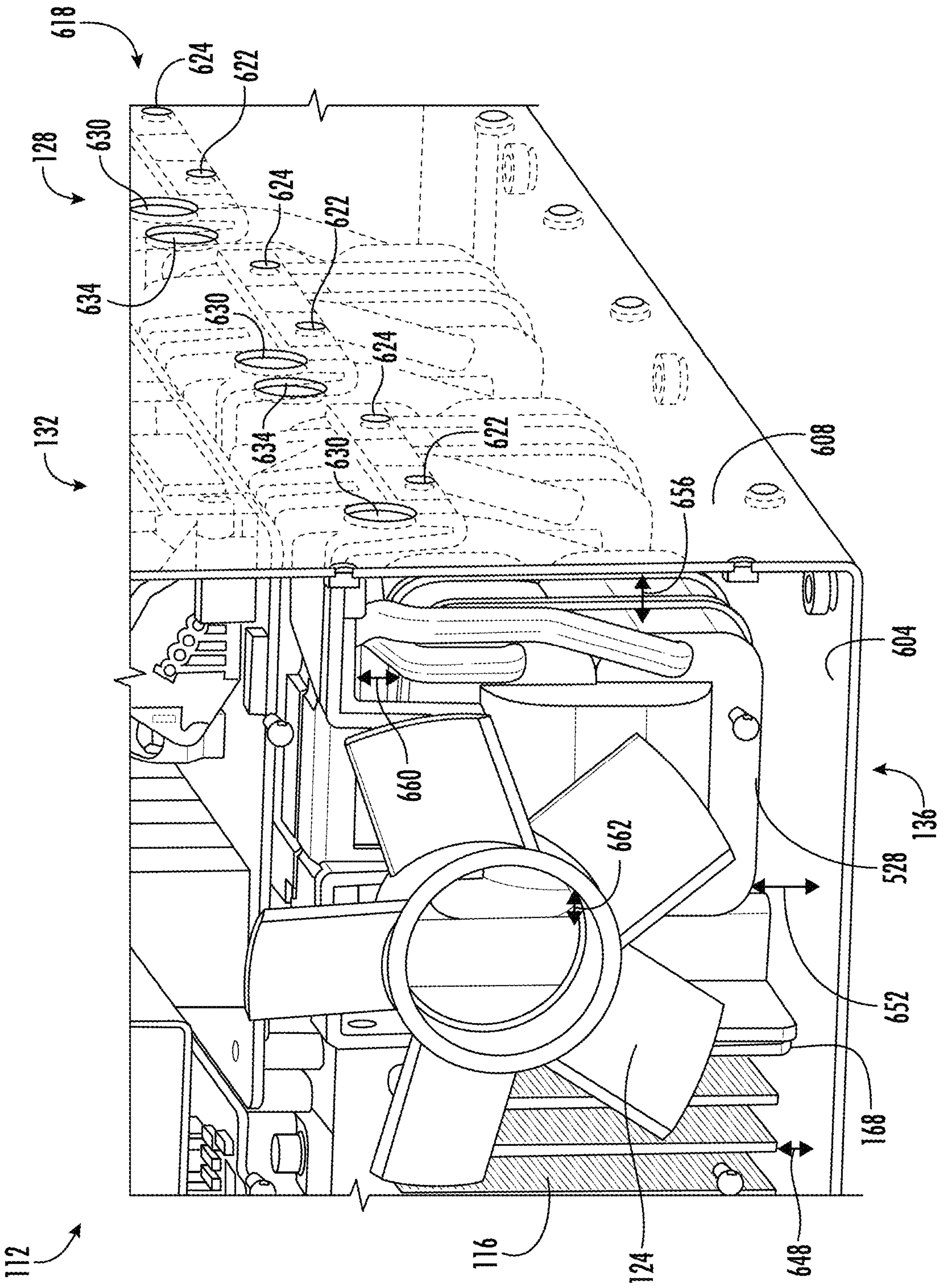
FIG. 18 is a perspective view of a portion of the X-ray generation unit of FIG. 1, according to an example embodiment.

The core mount 132 includes a longitudinal section 142 (e.g., first section, vertical portion, etc.) defining a first end 144 and a second end 148 extending along a first plane 152. The longitudinal section 142 includes a first planar portion 156 (e.g., first vertical portion, first flat section, etc.) extending along the first plane 152. The first planar portion 156 includes a first extension portion 158 (e.g., first flange, etc.) extending along the first end 144 of the longitudinal section 142. The first extension portion 158 is configured to receive a portion of the heat sink 116 to support the weight of the heat sink 116 and separate the heat sink 116 from a portion of the inner housing 112 (as shown in FIG. 18). The separation of the heat sink 116 from a portion of the inner housing 112 also acts as electrical insulation. The first planar portion 156 defines a first aperture 163 (e.g., opening, orifice, etc.) located closer to the second end 148 than the first end 144. The first aperture 163 is configured to receive a fastener to couple the assembly 128 to a portion of the inner housing 112 of the X-ray generation unit 110. The first planar portion 156 further defines a first channel 162 (e.g., groove, indentation, locating feature, etc.) (also shown in detail in FIG. 20). The first channel 162 extends from a midpoint of the first planar portion 156 along the second end 148 of the longitudinal section 142 toward the first end 144 of the longitudinal section 142. The first channel 162 extends towards a location closer to the second end 148 than the first end 144. The first channel 162 is configured to ensure constant thickness of the core mount 132 when the core mount 132 is injection molded.

Figure 19:
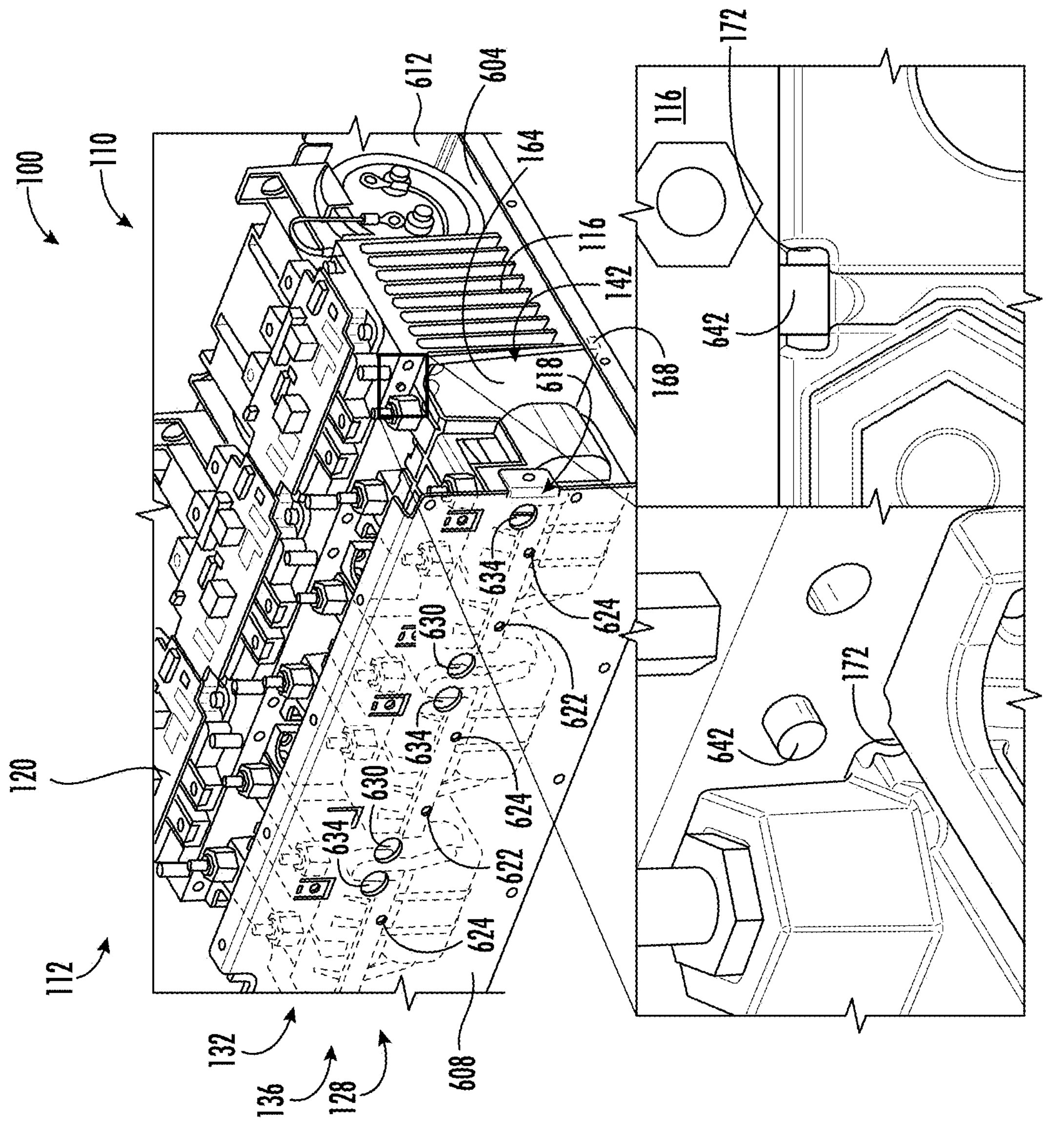
FIG. 19 is a perspective view and detailed views of the X-ray generation unit of FIG. 1, according to an example embodiment.

The longitudinal section 142 further includes a second planar portion 164 (e.g., second vertical portion, second flat section, etc.) extending along the first plane 152. The second planar portion 164 includes a second extension portion 168 (e.g., flange, etc.) extending along the first end 144 of the longitudinal section 142. The second extension portion 168 is configured to receive a portion of the heat sink 116 to support the weight of the heat sink 116 and separate the heat sink 116 from a portion of the inner housing 112 (as shown in FIG. 18). The second planar portion 164 also defines a second aperture 172 (e.g., opening, orifice, etc.) configured to receive an extension portion 642 extending from the heat sink 116 (as shown in FIG. 19) to couple the assembly 128 to a portion of the inner housing 112 of the X-ray generation unit 110. The second aperture 172 is located closer to the second end 148 than the first end 144 of the longitudinal section 142. The first planar portion 156 further defines a second channel 174 (e.g., groove, indentation, locating feature, etc.) (also shown in detail in FIG. 20.) The second channel 174 extends from a midpoint of the second planar portion 164 along the second end 148 of the longitudinal section 142 toward the first end 144 of the longitudinal section 142. The second channel 174 extends towards a location closer to the second end 148 than the first end 144. The second channel 174 is configured to receive an extension portion 642 extending from the heat sink 116 (as shown in FIG. 19). In the illustrated embodiment, the first channel 162 is a first width and the second channel 174 is a second width. The second width is greater than the first width. In other embodiments, the first width is greater than the second width. In other embodiments, the first width is substantially equal to the second width.

The longitudinal section 142 further includes a third planar portion 176 (e.g., third vertical portion, second flat section, etc.) parallel and offset to the first plane 152. The third planar portion 176 extends between the first planar portion 156 and the second planar portion 164. The third planar portion 176 is configured to prevent translation of the core assembly 136 in a direction of the longitudinal section 142 (e.g., along a y-axis, etc.). The third planar portion 176 includes a first tie aperture 180 (e.g., opening, orifice, etc.) a second tie aperture 182 (e.g., opening, orifice, etc.), a third tie aperture 184 (e.g., opening, orifice, etc.), and a fourth tie aperture 186 (e.g., opening, orifice, etc.). The first tie aperture 180 and the third tie aperture 184 are aligned (e.g., extend along an axis, etc.) along the third planar portion 176 and are configured to receive a first one of the ties 140. The second tie aperture 182 and the fourth tie aperture 186 are aligned (e.g., extend along an axis, etc.) along the third planar portion 176 and are configured to receive a second one of the ties 140. The ties 140 are configured to prevent translation of the core assembly 136 towards or away from the third planar portion 176 (e.g., along a z-direction, etc.) The first tie aperture 180 extends from the second end 148 of the longitudinal section 142 towards a location closer to the second end 148 than the first end 144. The second tie aperture 182 extends from the second end 148 of the longitudinal section 142 towards a location closer to the second end 148 than the first end 144. The third tie aperture 184 extends from the first end 144 towards a location closer to the first end 144 than the second end 148. The fourth tie aperture 186 extends from the first end 144 towards a location closer to the first end 144 than the second end 148.

In some embodiments, the third planar portion 176 may include more than two tie apertures (e.g., three tie apertures to receive three ties 140). In some embodiments the first planar portion may include less than two tie apertures (e.g., a single tie aperture, tie apertures are omitted when the core assembly 136 is coupled to the core mount 132 in an alternate fashion, etc.). The first tie aperture 180, the second tie aperture 182, the third tie aperture 184, and the fourth tie aperture 186 are configured to align the ties 140 so each of the ties 140 are parallel to each other (e.g., a first tie extends along a first axis and a second tie extends along a second axis, and the first axis is parallel to the second axis, etc.). In some embodiments, each of the ties 140 are at an oblique angle with respect to another tie 140 (e.g., a first tie extends along a first axis and a second tie extends along a second axis, and the first axis extends at an acute angle with respect to the second axis, etc.).

The longitudinal section 142 further includes a fourth planar portion 188 (e.g., vertical portion, flat portion, etc.) and a fifth planar portion 192 (e.g., vertical portion, flat section, etc.). The fourth planar portion 188 extends between the first planar portion 156 and the third planar portion 176. The fourth planar portion 188 extends substantially perpendicular to the first plane 152. The fifth planar portion 192 extends between the second planar portion 164 and the third planar portion 176. The fifth planar portion 192 extends substantially perpendicular to the first plane 152. The fifth planar portion 192 is substantially parallel to and offset from the fourth planar portion 188. The connection between fourth planar portion 188 and the first planar portion 156 defines a first curved edge 194 (e.g., arc, fillet, rounded edge, etc.), and the connection between the fifth planar portion 192 and the third planar portion 176 defines a second curved edge 198 (e.g., arc, fillet, rounded edge, etc.). In some embodiments, the first edge 194 and the second edge 198 are sharp corners.

Figure 20:
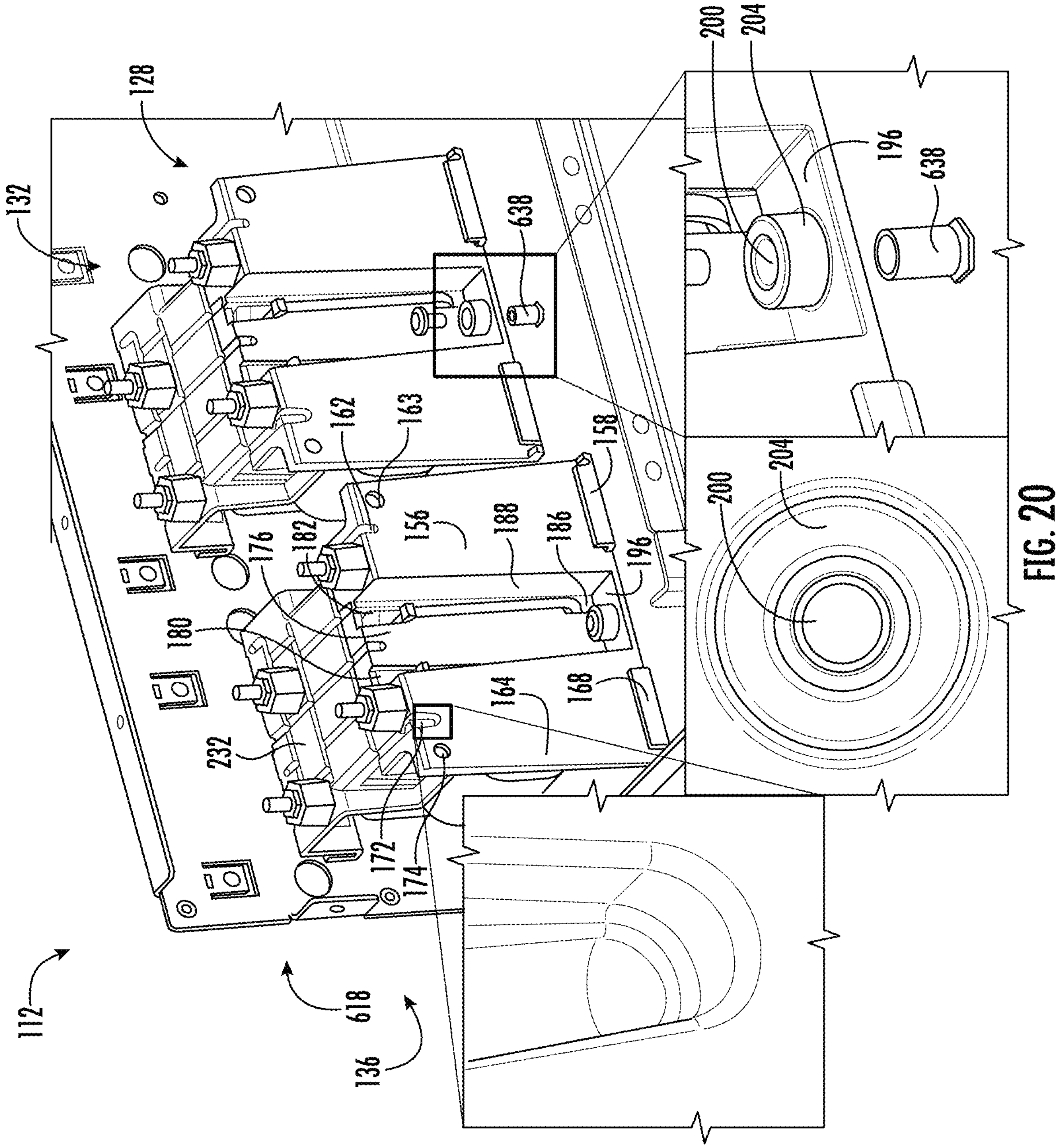
FIG. 20 is a perspective view and detailed views of a portion of the X-ray generation unit of FIG. 1, according to an example embodiment.

The longitudinal section 142 further includes a sixth planar portion 196 (e.g., horizontal portion, flat portion, etc.) located along the first end 144 of the longitudinal section 142. The sixth planar portion 196 extends between the first planar portion 156, the second planar portion 164, the third planar portion 176, the fourth planar portion 188, and the fifth planar portion 192. The sixth planar portion 196 extends perpendicular to the first plane 152. The sixth planar portion 196 defines an aperture 200 (e.g., orifice, opening, etc.) centered on the sixth planar portion 196 and an extrusion 204 (e.g., flange, etc.). The extrusion 204 extends from around the aperture 200 on the sixth planar portion 196 along a direction parallel to the first plane 152. The aperture 200 and the extrusion 204 are configured to couple to a portion of the inner housing 112 (as shown in FIG. 20).

The core mount 132 includes a lateral section 208 (e.g., horizontal section, etc.) defining a first end 212 and a second end 216. The lateral section 208 extends along a second plane 220, the second plane 220 substantially perpendicular to the first plane 152. The first end 212 of the lateral section 208 coincides with the second end 148 of the longitudinal section 142. The lateral section 208 further defines a core side 224 (e.g., internal side, etc.) and an external side 228 (e.g., outer side, second side, etc.). The core side 224 is opposite the external side 228, and is configured to confront the core assembly 136.

The lateral section 208 includes a planar portion 232 (e.g., flat portion, horizontal section, etc.). The planar portion 232 extends along the second plane 220 from the first end 212 of the lateral section 208 to an end 236 of the planar portion 232. The end 236 of the planar portion 232 is located closer to the second end 216 of the lateral section 208 than to the first end 212 of the lateral section 208. The planar portion 232 defines a first edge 240 (e.g., first side, first border, etc.) and a second edge 244 (e.g., second side, second border, etc.). The first edge 240 is opposite the second edge 244. The first edge 240 and the second edge 244 extend substantially perpendicular to the first end 212 and the second end 216 of the lateral section. The first channel 162 extends from the first end 212 of the planar portion 232 towards a location closer to the first end 212 of the lateral section than the second end 216 of the lateral section 208. The second channel 174 also extends from the first end 212 of the planar portion 232 towards a location closer to the first end 212 than the second end 216. The first channel 162 is located closer to the first edge 240 than the second edge 244, and the second channel 174 is located closer to the second edge 244 than the first edge 240.

The planar portion 232 further comprises a one or more core mounts 248 (e.g., core support, etc.). Each of the core mounts 248 is configured to contact the core assembly 136 to prevent the core assembly 136 from translating in a direction substantially parallel to the first plane 152 (e.g., in an x-direction, etc.). In the illustrated embodiment, the planar portion 232 includes a first core mount 252 and a second core mount 256. The first core mount 252 extends from the first edge 240 of the planar portion 232 along the core side 224 and the second core mount 256 extends from the second edge 244 of the planar portion 232 along the core side 224. The core mounts 248 are located at substantially a center portion of the first edge 240 and the second edge 244. In some embodiments, there may be more than two core mounts 248 or less than two core mounts 248. For example, there may be two core mounts 248 along the first edge 240 and one core mount 248 along the second edge 244. In another example, there may be one core mount 248 along the first edge 240 and the core mount 248 may be omitted from the second edge 244.

Each of the core mounts 248 includes a first mount section 300 (e.g., first portion, vertical portion, etc.), a second mount section 304 (e.g., second portion, horizontal portion, etc.), and a third mount section 308 (e.g., third portion, vertical portion, etc.). The first mount section 300 of the first core mount 252 extends away from the first edge 240 of the planar portion 232. The first mount section 300 of the second core mount 256 extends away from the second edge 244 of the planar portion 232. The first mount section 300 is substantially perpendicular to the second plane 220. The second mount section 304 extends from the first mount section 300 away from the longitudinal section 142. The second mount section 304 is substantially perpendicular to the first mount section 300 and substantially parallel to the second plane 220. The third mount section 308 of the first core mount 252 extends between the second mount section 304 and the first edge 240 of the planar portion 232. The third mount section 308 of the second core mount 256 extends between the second mount section 304 and the second edge 244 of the planar portion 232. The third mount section 308 is substantially parallel to the first mount section 300, substantially perpendicular to the second mount section 304, and substantially perpendicular to the second plane 220.

The planar portion 232 further comprises a plurality of receptacles 312 (e.g., flange, etc.) extending between a first end 320 and a second end 316 of the receptacle 312. In the illustrated embodiment, there are four receptacles 312. A first receptacle 313 and a second receptacle 314 are located closer to the first edge 240 than the second edge 244. A third receptacle 315 and a fourth receptacle 317 are located closer to the second edge 244 than to the first edge 240. The first receptacle 313 and the third receptacle 315 are located closer to the first end 212 of the lateral section 208 than the second end 216 of the lateral section 208. The second receptacle 314 and the fourth receptacle 317 are located closer to the second end 216 of the lateral section 208 than the first end 212 of the lateral section 208. The first receptacle 313 aligns with the third receptacle 315 and the second receptacle 314 aligns with the fourth receptacle 317. In other embodiments there may be more or less than four receptacles 312 (e.g., three, six, etc.) and the location of the receptacles 312 may be include alternate positional relationships (e.g., all four receptacles 312 may be located closer to the second edge 244 than to the first edge 240, etc.)

The first end 320 of each the receptacles 312 is located along the planar portion 232, and the second end 316 is parallel and offset from the second plane 220. Each of the receptacles 312 includes an aperture 324 (e.g., receptacle aperture, orifice, etc.) extending through planar portion 232 configured to receive a portion of the core assembly 136. In the example embodiment, there are four receptacles 312 and four apertures 324.

Each of the apertures 324 includes a plurality of sides 328 (e.g., edge, border, etc.). In the illustrated embodiment, the plurality of sides 328 form a hexagon cross sectional area. The hexagon cross sectional area are advantageous for standoff blind screwing, since the cross sectional area aids in maintaining alignment during assembly and minimizes rotation of a standoff while tightening the standoff. In some embodiments, the plurality of sides 328 form a polygon cross-sectional area (e.g., triangle, hexagon, octagon, quadrilateral, etc.). In some embodiments, the plurality of sides 328 are curved to form a non-polygon cross sectional area (e.g., circular, ellipsoid, etc.).

Figure 21:
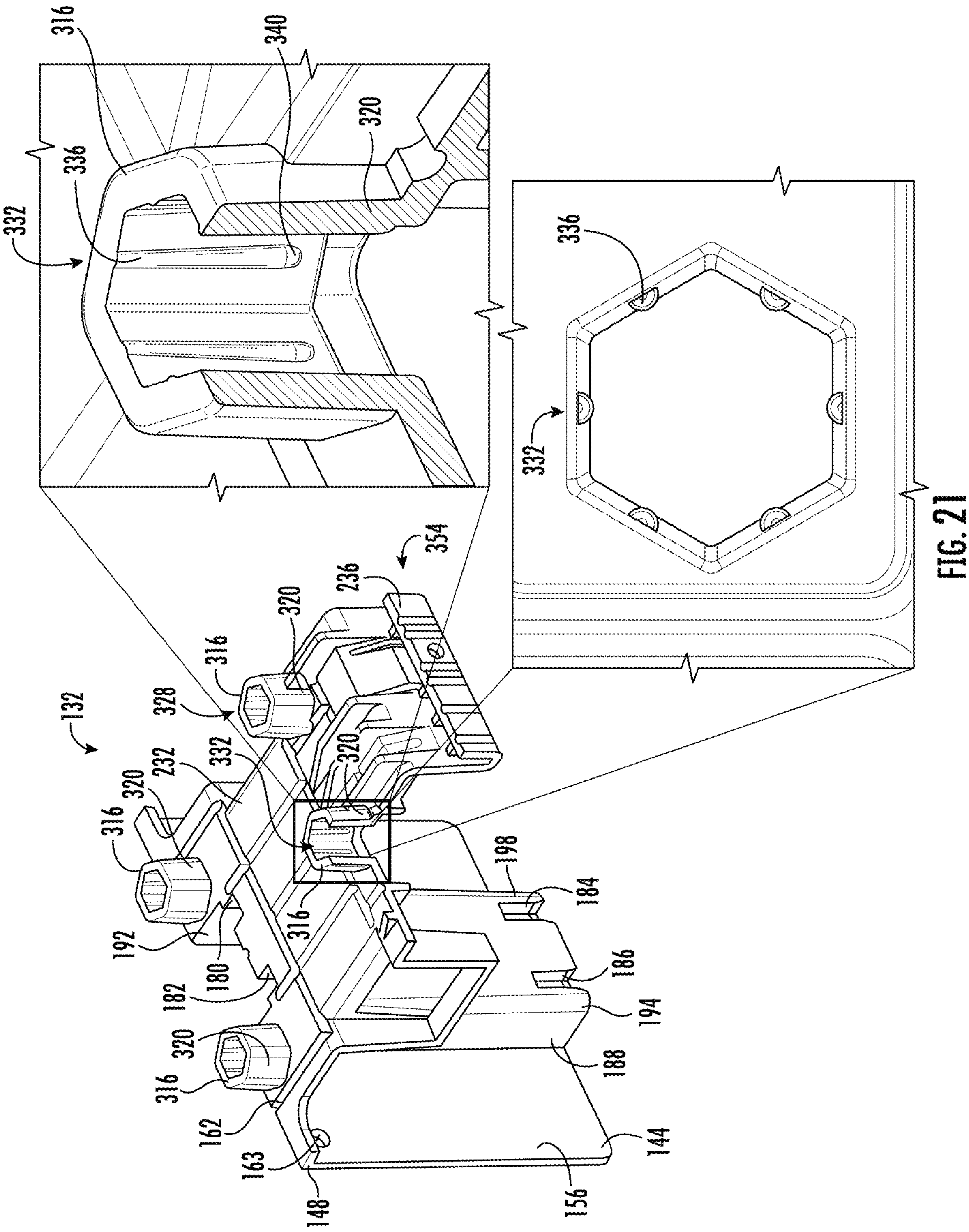
FIG. 21 is a perspective view, a cross sectional view, and a detail view of a portion of the core mount of FIG. 3, according to an example embodiment.

As shown in FIG. 21, each of the sides 328 includes a protrusion 332 (e.g., location feature, nub, projection, bulge, etc.) extending between a first end 340 of the protrusion 332 and a second end 336 of the protrusion 332 (as shown in FIG. 21). The protrusions 332 are configured to prevent a portion of the core assembly 136 from rotating within the receptacles 312. In some embodiments, protrusions are omitted from some of the sides 328 (e.g., every other side 328 includes a protrusion 332, etc.). The protrusion 332 forms a portion of a cylinder. In some embodiments, the protrusion 332 may form a portion of a polygon (e.g., triangle, hexagon, octagon, quadrilateral, etc.). The protrusion 332 extends from the second end 316 of the receptacle 312 towards a location closer to the first end 320 of the receptacle 312 than the second end 316 of the receptacle 312. The second end 336 of the protrusion 332 is located at the second end 316 of the receptacle 312. The first end 340 of the protrusion 332 forms a first width and the second end 336 of the protrusion 332 forms a second width. The first width is greater than the second width.

The lateral section 208 further comprises a lateral section extension portion 344 (e.g., planer section flange, etc.). The lateral section extension portion 344 extends from the end 236 of the planar portion 232 to the second end 216 of the lateral section 208. The lateral section extension portion 344 includes a first portion 348 extending from the planar portion 232 and a second portion 352 extending from the first portion 348. The first portion 348 extends at an oblique angle with respect to the planar portion 232. The second portion 352 is substantially parallel to the first plane 152. In some embodiments, the second portion 352 extends at an oblique angle with respect to the first plane 152. In some embodiments, the first portion 348 extends at a right angle with respect to the planar portion 232. The first portion 348 extends in a first direction, and the second portion 352 extends in a second direction, the second direction opposite the first direction. Each of the first portion 348 and the second portion 352 define a plurality of apertures 354 configured to receive a fastener (as shown in FIGS. 13-14).

Figure 13:
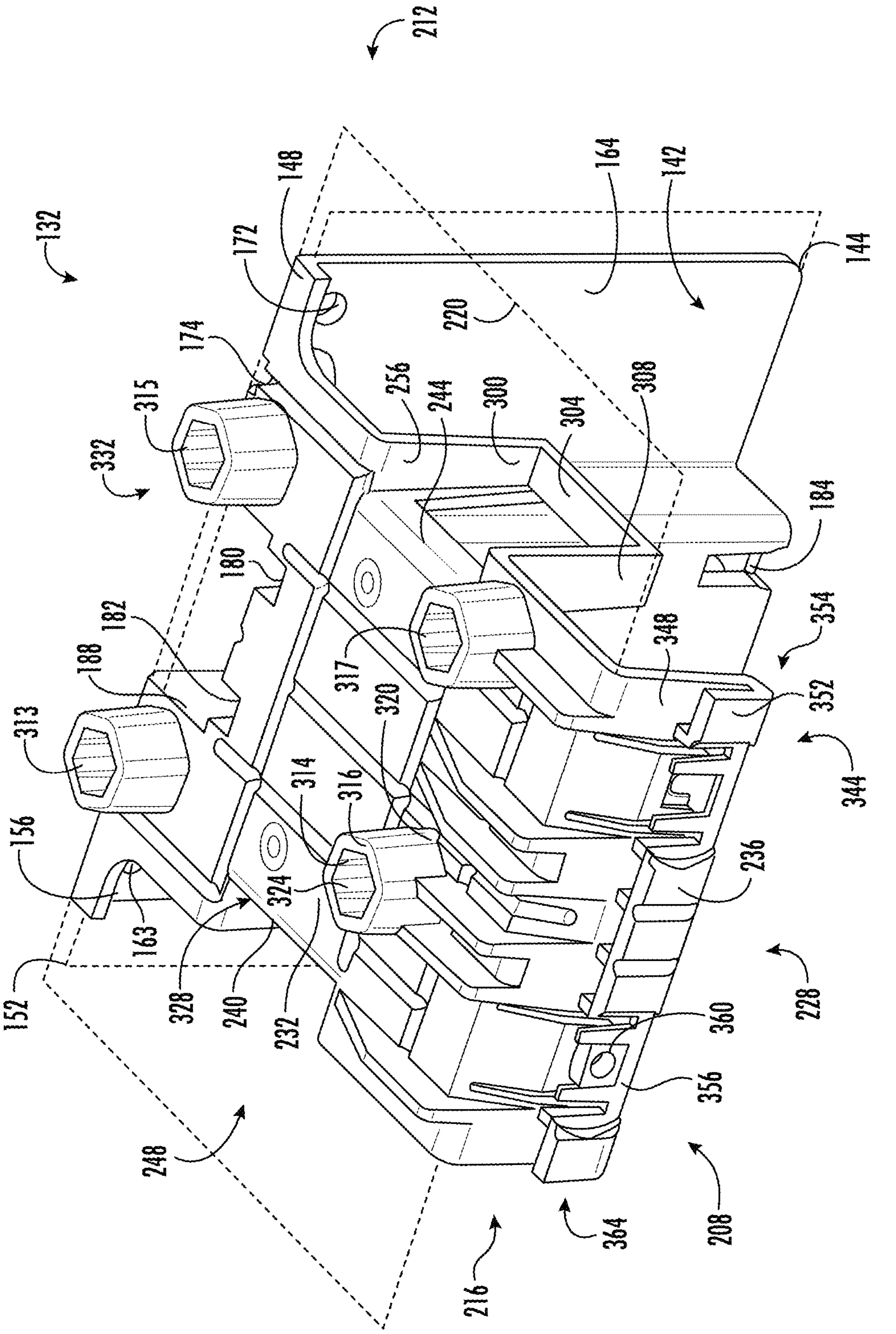
FIG. 13 is a perspective view of the core mount of FIG. 3, according to an example embodiment.
Figure 14:
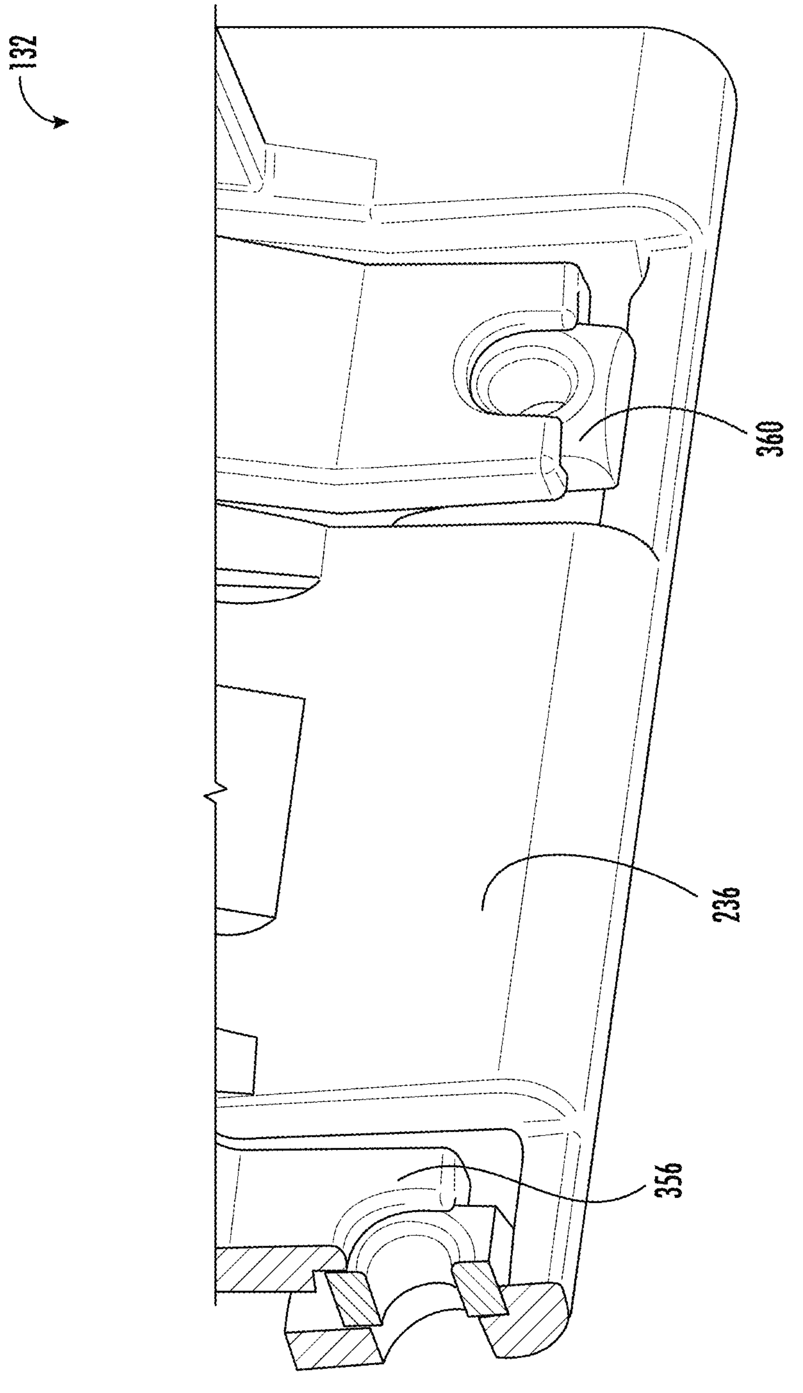
FIG. 14 is a perspective view of a portion of the core mount of FIG. 13, according to an example embodiment.

As shown in the partial cross-section view of FIGS. 13-14, the lateral section extension portion 344 contains compartments 356 (e.g., enclosures, etc.) configured to receive nuts 360. In the illustrated embodiment, the nuts 360 are square nuts. In the illustrated embodiment of FIG. 13, the compartments 356 include a plurality of prongs 364 (e.g., prongs, partitions, etc.) extending parallel to the first plane 152. Neighboring prongs 364 create gaps configured to receive one of the nuts 360. The nuts 360 are each received within the compartments 356 with a snap fit. The snap fit provides for a faster assembly without additional fasteners, allowing for a more convent and efficient assembly. The nuts 360 align with the apertures 354 defined in the first portion 348 and the second portion 352.

Referring now to FIGS. 1-8, the core assembly 136 comprises a magnetic core 368 (e.g., core, nucleus, etc.) comprising a core body 504 (e.g., unit, etc.) and a protective coating 508 (e.g., layer, finish, covering, film, etc.). The magnetic core 368 is configured to create strong and uniform magnetic fields, contributes to field stabilization, and directs magnetic flux. The magnetic core 368 may also assist in optimizing energy usage by reducing resistance in the X-ray generation unit 110. The magnetic core 368 is covered by the protective coating 508 (e.g., the protective coating 508 is applied to the magnetic core 368, etc.). The protective coating 508 is configured to protect the magnetic core 368 from environment factors (e.g., moisture, dust, mechanical wear, etc.) and improve electrical insulation. The core body 504 defines a first side 512, a second side 516, a third side 520, a fourth side 524, a fifth side 528, and a sixth side 532. The first side 512 is substantially parallel to the third side 520, and the first side 512 is perpendicular to the second side 516. The fifth side 528 is substantially parallel to the second side 516, the fourth side 524 is substantially parallel to the sixth side 532. The fourth side 524 extends between the fifth side 528, the first side 512, the third side 520, and the second side 516. The first side 512 extends substantially perpendicular to the second plane 220. And the second side 516 is offset from the second plane 220. The third side 520 is opposite the first side 512. The ties 140 are coupled to the fourth side 524 of the magnetic core 368. In some embodiments, the magnetic core 368 defines more or less than six sides (e.g., 8 sides, 10 sides, etc.).

The core assembly 136 includes a plurality of insulated cables 536 (e.g., coated cables, insulated wires, etc.). The plurality of insulated cables 536 includes a first cable 540 (e.g., wire, etc.), a second cable 544 (e.g., wire, etc.), a third cable 548 (e.g., wire, etc.), and a fourth cable 552 (e.g., wire, etc.) electrically coupled to the magnetic core 368. The first cable 540 includes a first portion 554 and a second portion 556. The first portion 554 of the first cable 540 extends from the first side 512 of the magnetic core 368 to the second side 516 of the magnetic core 368. The second portion 556 of the first cable 540 extends along the second side 516 of the magnetic core 368. The second cable 544 includes a first portion 560 and a second portion 564. The first portion 560 of the second cable 544 extends from the first side 512 of the magnetic core 368 to the second side 516 of the magnetic core 368. The second portion 564 of the second cable 544 extends along the second side 516 of the magnetic core 368.

The third cable 548 includes a first portion 568 and a second portion 572. The first portion 568 of the third cable 548 extends from the third side 520 of the magnetic core 368 to the second side 516 of the magnetic core 368. The second portion 572 of the third cable 548 extends along the second side 516 of the magnetic core 368. The fourth cable 552 includes a first portion 576 and a second portion 580. The first portion 576 of the fourth cable 552 extends from the third side 520 of the magnetic core 368 to the second side 516 of the magnetic core 368. The second portion 580 of the fourth cable 552 extends along the second side 516 of the magnetic core 368.

The core assembly 136 further comprises a plurality of standoffs 584 (e.g., spacers, mounts, etc.). Standoffs 584 sometimes reach high temperatures, and therefore in embodiments where the standoffs 584 are plastic, standoffs 584 are designed to withstand high temperatures to resist melting and deformation. The standoffs 584 as described herein withstand temperatures of 75° C. and may support temperatures of up to 105° C. In the present embodiment, the standoffs 584 are made of Norl N1050, which has a UL94 V0 rating. The highest temperature in the system is set to be the level of the standoffs 584, since the insulated cables 536 are insulated and are therefore a lower temperature than the standoffs 584. In other embodiments, the standoffs 584 can be created from other materials which may withstand high temperatures (e.g., polycarbonate, nylon, polyphenylene sulfide, polyetherimide, etc.). Each of the standoffs 584 is configured to couple to an end of one of the cables 536. The plurality of standoffs 584 includes a first standoff 588 (e.g., spacer, mount, etc.), a second standoff 592 (e.g., spacer, mount, etc.), a third standoff 596 (e.g., spacer, mount, etc.), and a fourth standoff 600 (e.g., spacer, mount, etc.). The first standoff 588 couples to the first cable 540, the second standoff 592 couples to the second cable 544, the third standoff 596 couples to the third cable 548, and the fourth standoff 600 couples to the fourth cable 552. In some embodiment, the plurality of standoffs 584 may include more or less than four standoffs 584 (e.g., two standoffs, one standoff, etc.).

In the illustrated embodiment, the insulated cables 536 are 2.24 mm copper wire with an antioxidant sheath. A portion (e.g., 2 cm, etc.) of the antioxidant sheath is removed from an end of the insulated cable 536, and the end of the insulated cable 536 is folded back onto the insulated cable 536. Each of the insulated cables 536 is then inserted into one of the standoffs 584, and each of the insulated cables 536 are braised in the standoff 584. The insulated cable 536 is then set back into a thermal sheath and bent within a custom jig. The insulated cable 536 and the standoffs 584 are then coupled within the core mount 132.

Referring now to FIGS. 2-7, The first standoff 588 is configured to be received within the aperture 324 of the first receptacle 313, the second standoff 592 is configured to be received within the aperture 324 of the fourth receptacle 317, the third standoff 596 is configured to be received within the aperture 324 of the first receptacle 313, and the fourth standoff 600 is configured to be received within the aperture 324 of the third receptacle 315. The first side 512 of the core assembly 136 is configured to couple to the first core mount 252 and the third side 520 of the core assembly 136 is configured to couple to the second core mount 256. The second side 516 of the core assembly 136 is configured to confront the core side 224 of the lateral section 208. The sixth side 532 of the core assembly 136 is configured to confront the longitudinal section 142. The protrusions 332 are configured to prevent the standoffs 584 from rotating.

Referring now to FIGS. 15-20, the X-ray generation unit 110 including the assembly 128. The inner housing 112 defines a lateral piece of sheet metal 604 (e.g., a first mount material, a lateral mounting material, etc.), a first longitudinal piece of sheet metal 608 (e.g., a longitudinal mount material, a mounting sheet, etc.), and a second longitudinal piece of sheet metal 612 (e.g., a longitudinal mount material, a mounting sheet, etc.). The first longitudinal piece of sheet metal 608 extends parallel to the second longitudinal piece of sheet metal 612, and the first lateral piece of sheet metal 604 extends between the first longitudinal piece of sheet metal 608 and the second longitudinal piece of sheet metal 612. The first longitudinal piece of sheet metal 608 extends parallel to the first plane 152 and the lateral piece of sheet metal 604 extends parallel to the second plane 220. In the illustrated embodiment, the lateral piece of sheet metal 604, the first longitudinal piece of sheet metal 608, and the second longitudinal piece of sheet metal 612 are metal. In other embodiments, the lateral piece of sheet metal 604, the first longitudinal piece of sheet metal 608, and the second longitudinal piece of sheet metal 612 may be formed of an alternate material (e.g., plastic, etc.).

The first longitudinal piece of sheet metal 608 is configured to contact the second portion 352 of the extension portion 344 of lateral section 208. The first longitudinal piece of sheet metal 608 defines a plurality of apertures 618 (e.g., orifices, openings, etc.). The plurality of apertures 618 defines a first aperture 622 (e.g., orifice, opening, etc.), and a second aperture 624 (e.g., orifice, opening, etc.). The first aperture 622 is configured to align with one of the apertures 354 in the lateral section extension portion 344 and therefore align with one of the nuts 360. The second aperture 624 is configured to align with one of the apertures 354 in the lateral section extension portion 344 and therefore align with one of the nuts 360. A fastener may be inserted into the first aperture 622, one of the apertures 354, and one of the nuts 360 to couple the first longitudinal piece of sheet metal 608 to the assembly 128. A fastener may also be inserted into the second aperture 624, one of the apertures 354, and one of the nuts 360 to couple the first longitudinal piece of sheet metal 608 to the assembly 128.

The plurality of apertures 618 of the first longitudinal piece of sheet metal 608 further defines a third aperture 630 (e.g., orifice, opening, etc.) and a fourth aperture 634 (e.g., orifice, opening, etc.). The third aperture 630 and the fourth aperture 634 are configured to allow for insertion of a tightening mechanism (e.g., a screw driver, etc.). The third aperture 630 of the first longitudinal piece of sheet metal 608 aligns with the first aperture 163 of the first planar portion 156 of the longitudinal section 142. The fourth aperture 634 of the first longitudinal piece of sheet metal 608 is configured to align with the second aperture 172 defined by the second planar portion 164 of the longitudinal section. A fastener and the tightening mechanism are inserted through one of the third aperture 630 or the fourth aperture 634, and the core mount 132 is coupled to the heat sink 116.

The lateral piece of sheet metal 604 includes a mount 638 (e.g., stand, platform, support, etc.), as shown in FIG. 20. The mount 638 extends away from the lateral piece of sheet metal 604 and is parallel to the first longitudinal piece of sheet metal 608. The mount 638 is configured to align with and receive the aperture 200 defined by the sixth planar portion 196 of the longitudinal section 142 of the core mount 132. As shown in FIG. 20, the mount 638 is aligned with the aperture 200 and the core mount 132 is placed on the lateral piece of sheet metal 604. The aperture 200 and the mount 638 are configured to receive a fastener to maintain alignment between the lateral piece of sheet metal 604 and the core mount 132. The connection of the mount 638 with the aperture 200 increases the level of precision when assembling the X-ray generation unit 110 and increases the uniformity between X-ray generation units 110, since the mount 638 is aligned with and received within the first aperture 200.

The heat sink 116 includes one or more extension portions 642 (e.g., locating features, flanges, etc.), as shown in FIG. 19. Each extension portion 642 is configured to align with one of the first channel 162 or the second channel 174 on the longitudinal section 142. As shown in FIG. 19, the heat sink 116 is lowered toward the lateral piece of sheet metal 604. The extension portion 642 is retained within the first channel 162 or the second channel 174. The connection of the first channel 162 or the second channel 174 with the extension portions 642 increases the level of precision when assembling the X-ray generation unit 110 and increases the uniformity between X-ray generation units 110, since the extension portion 642 is aligned with and received within the first channel 162 or the second channel 174. The first channel 162 and the second channel 174 also support the weight of the heat sink 116 and assist in preventing the heat sink 116 from contacting the lateral piece of sheet metal 604.

Figure 16:
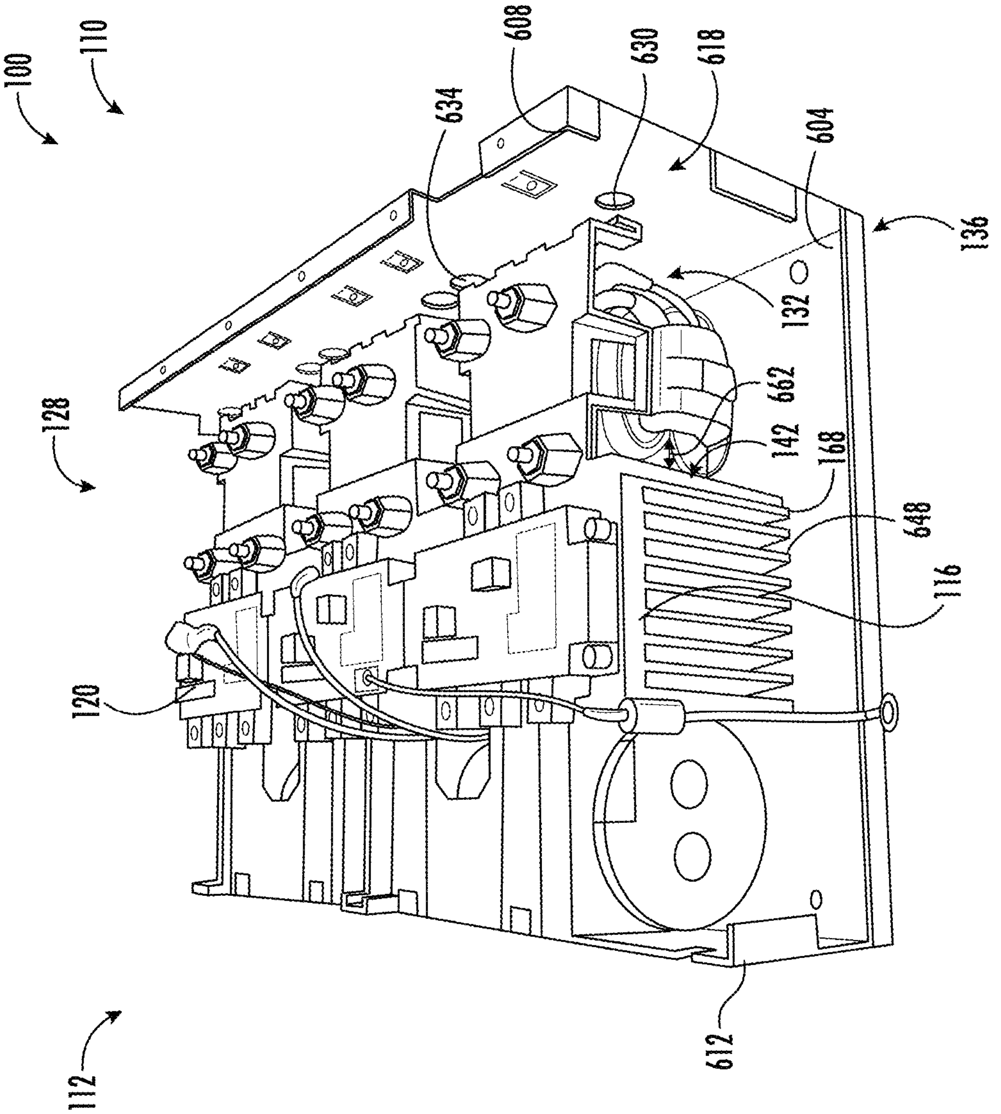
FIG. 16 is another perspective view of the X-ray generation unit of FIG. 1, according to an example embodiment.
Figure 17:
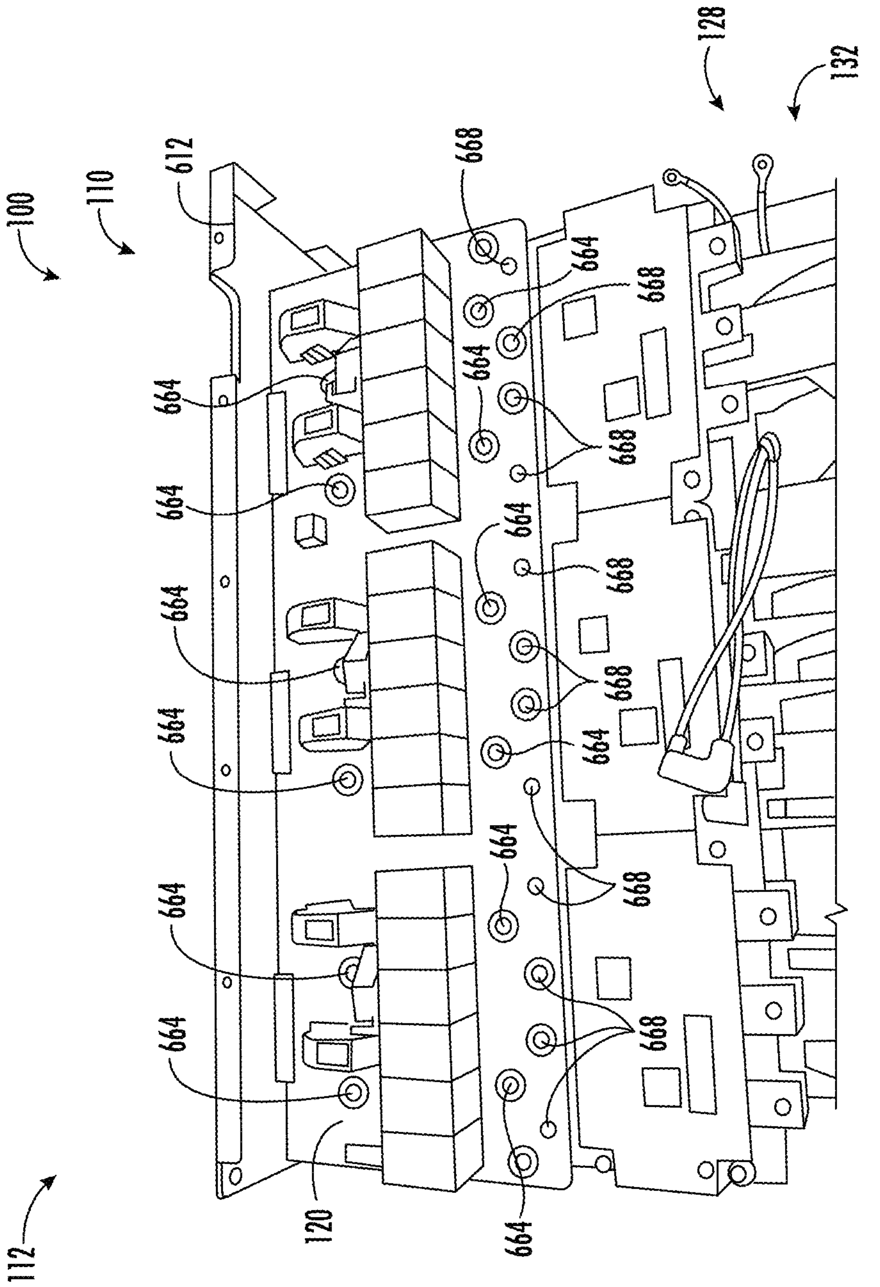
FIG. 17 is a top view of the X-ray generation unit of FIG. 1, according to an example embodiment.

The heat sink 116 is upheld by the extension portions 642 to form a first gap 648 between the heat sink 116 and the lateral piece of sheet metal 604. As described previously, the first extension portion 158 and the second extension portion 168 are also configured to contact a portion of the heat sink 116 to form the first gap 648 between the heat sink 116 and the lateral piece of sheet metal 604 (as shown in FIGS. 16, and 18-19). The first gap 648 is configured to accommodate thermal expansion and improve airflow around the heat sink 116. In the illustrated embodiment, the heat sink 116 maintains a distance of 5 mm from the lateral piece of sheet metal 604. In other embodiments, this distance is more or less than 5 mm (e.g., 3 mm, 10 mm, etc.). The distance may be altered in accordance with space constraints or measured temperatures. The first gap 648 allows the heat sink 116 to maintain a first voltage and the lateral piece of sheet metal 604, the first longitudinal piece of sheet metal 608, and the second longitudinal piece of sheet metal 612 to maintain a second voltage, the first voltage different than the second voltage. In some embodiments, the first voltage and the second voltage are substantially equal.

As shown in FIG. 18, the fan 124 is coupled within the inner housing 112. The fan 124 is configured to increase air flow in a direction parallel to the fourth side 524 of the core assembly 136. The air flow is also perpendicular to the first side 512 the third side 520 of the core assembly 136. A second gap 652 is formed between the fifth side 528 of the core assembly 136 and the lateral piece of sheet metal 604, a third gap 656 is formed between the fourth side 524 of the core assembly 136 and the first longitudinal piece of sheet metal 608, a fourth gap 660 is formed between the second side 516 of the core assembly 136 and the lateral section 208, and a fifth gap 662 is formed between the sixth side 532 and the longitudinal section 142 (as shown in FIG. 16). Each of the second gap 652, the third gap 656, the fourth gap 660, the fifth gap 662 is configured to allow air flow to pass over the magnetic core 368 and allow a high surface area of the magnetic core 368 to be in contact with air flow. Each of the gaps allows the air flow to be in contact with the majority of the sides of the magnetic core 368, increasing cooling of the magnetic core 368.

Figure 15:
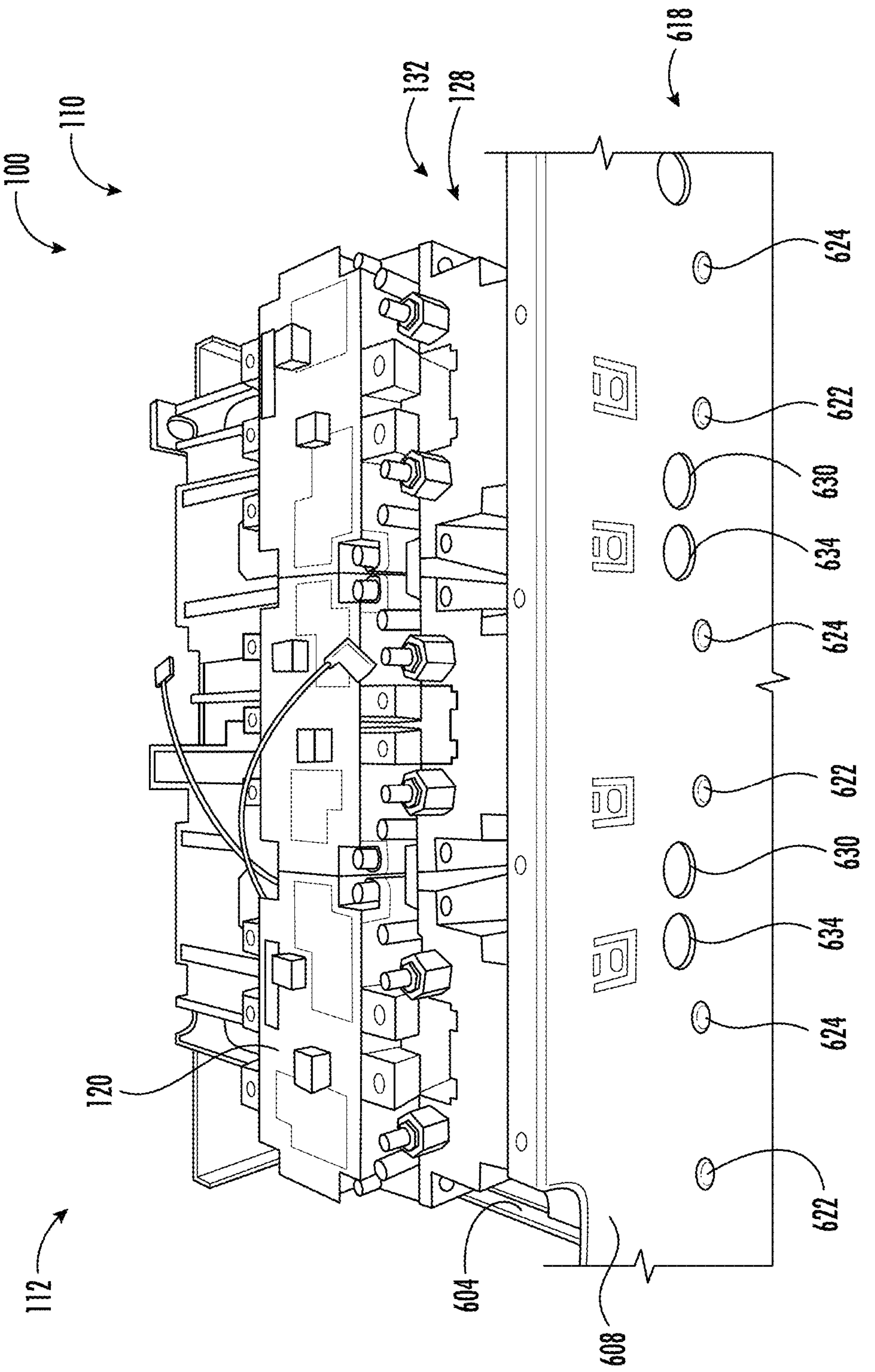
FIG. 15 is a perspective view of the X-ray generation unit of FIG. 1, according to an example embodiment.

Referring now to FIG. 15, the circuit board 120 is coupled to the heat sink 116 opposite the lateral piece of sheet metal 604. The circuit board 120 is substantially parallel to the lateral piece of sheet metal 604. The circuit board 120 comprises a plurality of first circuit board apertures 664 and a plurality of second circuit board apertures 668. The plurality of first circuit board apertures 664 are located closer to a center of the circuit board 120 than the second circuit board apertures 668. In the illustrated embodiment, the first circuit board apertures 664 includes twelve 7 mm diameter holes. The first circuit board apertures 664 are configured to receive twelve M6 standoffs and the second circuit board apertures 668 are configured to receive coupling mechanisms to couple the circuit board 120 to the heat sink 116. Nuts may be coupled to the coupling mechanisms or fasteners on a side of the circuit board 120 farthest from the lateral piece of sheet metal 604, since a side of the circuit board closest to the lateral piece of sheet metal 604 is blocked from receiving nuts by the heat sink 116. The amount of first circuit board apertures 664 and second circuit board apertures 668 also reduces any gap between the circuit board 120 and the heat sink 116, increasing the compactness of the X-ray generation unit 110.

The embodiments described herein have been described with reference to drawings. The drawings illustrate certain details of specific embodiments that provide the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As utilized herein, terms of degree such as "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that terms such as "exemplary," "example," and similar terms, as used herein to describe various embodiments, are intended to indicate that such embodiments are possible examples, representations, or illustrations of possible embodiments, and such terms are not intended to connote that such embodiments are necessarily extraordinary or superlative examples.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any element on its own or any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the drawings. It should be noted that the orientation of various elements may differ according to other exemplary embodiments, and that such variations are intended to be encompassed by the present disclosure.

Although the drawings may show and the description may describe a specific order and composition of method steps, the order of such steps may differ from what is depicted and described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variation may depend on designer choice. All such variations are within the scope of the disclosure.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions, and arrangement of the embodiments without departing from the scope of the present disclosure as expressed in the appended claims.

What is claimed is:

1. An assembly configured for use in an X-ray generation unit of a medical imaging device, the assembly comprising:

- a core assembly comprising:
  - a magnetic core;
  - a plurality of insulated cables configured to electrically couple to the magnetic core; and
  - a plurality of standoffs, each of the standoffs configured to couple to an end of each of the insulated cables;
- a core mount configured to receive the core assembly, the core mount comprising:
  - a longitudinal section extending along a first plane;
  - a lateral section extending from the longitudinal section along a second plane; and
  - a plurality of receptacles extending from the lateral section, each of the receptacles substantially perpendicular to the second plane, each of the receptacles comprising a receptacle aperture configured to receive one of the standoffs; and
- one or more ties configured to couple the core assembly to the core mount.

2. The assembly of claim 1, wherein:

- each of the receptacles forms a plurality of sides, each of the sides comprising a protrusion extending from a first end of the receptacle to a location closer to a second end of the receptacle than the first end of the receptacle, the protrusion configured to prevent the standoff from rotating; and
- each of the receptacles forms a polygon cross-section.

3. The assembly of claim 2, wherein:

- the protrusion is a first width at a first end of the protrusion and a second width at a second end of the protrusion;
- the second width greater than the first width;
- the first end of the protrusion is located at the first end of the receptacle; and
- the standoff is configured to be inserted into the first end of the receptacle.

4. The assembly of claim 1, wherein the lateral section of the core mount further comprises:

- a planar portion extending from the longitudinal section along the second plane, the planar portion comprising:
  - a core side; and
  - an external side opposite the core side; and
- one or more core mounts configured to couple to the magnetic core, each of the core mounts comprising:
  - a first mount section extending from the core side of the planar portion away from the external side of the planar portion;
  - a second mount section extending from the first mount section away from the longitudinal section; and
  - a third mount section extending between the second mount section and the core side of the planar portion.

5. The assembly of claim 4, wherein a first core mount is located along a first edge of the planar portion and a second core mount is located along a second edge of the planar portion, the first edge opposite the second edge.

6. The assembly of claim 1, wherein the longitudinal section comprises:

- a planar portion offset from the first plane, the planar portion configured to restrict translation of the magnetic core, the planar portion comprising:
  - a first tie aperture configured to receive one of the ties, the first tie aperture located along a first end of the planar portion; and
  - a second tie aperture configured to receive one of the ties, the second tie aperture located along a second end of the planar portion, the second end opposite the first end.

7. The assembly of claim 1, wherein the medical imaging device is an X-ray imaging device, the magnetic core is a high-power magnetic core, and the magnetic core comprises:

- a core body; and
- a protective coating applied to the core body.

8. The assembly of claim 1, wherein:
the lateral section comprises:
a planar portion extending along the second plane; and
an extension portion extending from the planar portion, the extension portion extending at an oblique angle to the planar portion, the extension portion comprising:
one or more compartments, and
one or more nuts, each nut configured to be received within one of the compartments, the nut configured to receive a fastener to couple the core mount to a piece of sheet metal.

9. The assembly of claim 1, wherein:
the plurality of insulated cables comprises:
a first cable comprising:
a first portion extending from a first side of the magnetic core to a second side of the magnetic core; and
a second portion extending along the second side of the magnetic core;
a second cable comprising:
a first portion extending from the first side of the magnetic core to the second side of the magnetic core; and
a second portion extending along the second side of the magnetic core;
a third cable comprising:
a first portion extending from a third side of the magnetic core to the second side of the magnetic core; and
a second portion extending along the second side of the magnetic core; and
a fourth cable comprising:
a first portion extending from the third side of the magnetic core to the second side of the magnetic core; and
a second portion extending along the second side of the magnetic core;
wherein the first side of the magnetic core extends perpendicular to the second plane, the second side of the magnetic core is offset from the second plane, and the third side of the magnetic core is opposite the first side of the magnetic core.

10. The assembly of claim 9, wherein one tie of the one or more ties is coupled to a fourth side of the magnetic core, the fourth side of the magnetic core extending between the first side of the magnetic core and the third side of the magnetic core.

11. The assembly of claim 1, wherein:
the longitudinal section comprises:
a planar portion extending along the first plane; and
an extension portion extending from the planar portion perpendicular to the first plane, the extension portion extending along a first direction, the extension portion configured to contact a longitudinal piece of sheet metal; and
the lateral section extends along a second direction, the first direction opposite the second direction.

12. The assembly of claim 11, wherein:
the planar portion is a first planar portion, and the first planar portion includes a first aperture;
the extension portion is a first extension portion;
the longitudinal section further comprises:
a second planar portion offset from the first plane;
a third planar portion extending along the first plane, the third planar portion including a second aperture; and
a second extension portion extending from the third planar portion perpendicular to the first plane, the extension portion extending along the first direction; and
the second planar portion extends between the first planar portion and the third planar portion and the first aperture and the second aperture are configured to receive fasteners to couple the core mount to a heat sink.

13. The assembly of claim 12, wherein:
the longitudinal section further comprises:
a fifth planar portion extending between the first planar portion, the second planar portion, and the third planar portion, the fifth planar portion offset from the second plane, the fifth planar portion including an aperture configured to receive a fastener to couple the core mount to the longitudinal piece of sheet metal.

14. The assembly of claim 12, further comprising:
a lateral piece of sheet metal extending parallel to the first plane, the lateral piece of sheet metal comprising:
a third aperture configured to align with the first aperture; and
a fourth aperture configured to align with the second aperture.

15. The assembly of claim 1, wherein:
the lateral section extends between a first end and a second end; and
the lateral section further comprises a planar portion extending along the second plane, the planar portion extending from the first end towards the second end, the planar portion including:
a channel extending from the first end towards a location closer to the first end than the second end, the channel configured to receive a fastener extending from a heat sink.

16. The assembly of claim 15, wherein:
the longitudinal section extends between a first end and a second end;
the second end of the longitudinal section coincides with the first end of the lateral section; and
the channel extends from the second end of the longitudinal section towards a location closer to the second end of the longitudinal section than the first end of the longitudinal section.

17. The assembly of claim 1, wherein the core mount forms an L-shaped side profile.

18. The assembly of claim 1, wherein the assembly further comprises:
a longitudinal piece of sheet metal coupled to the lateral section of the core mount;
a lateral piece of sheet metal extending from the longitudinal piece of sheet metal; and
a heat sink coupled to the lateral section of the core mount;
wherein a gap is formed between the lateral piece of sheet metal and the heat sink.

19. An assembly for use in an X-ray generation unit of a medical imaging device, the assembly comprising:
a core assembly comprising:
a magnetic core;
a plurality of insulated cables configured to electrically couple to the magnetic core; and
a plurality of standoffs, each of the standoffs configured to couple to an end of each of the insulated cables; and
a core mount configured to receive the core assembly, the core mount comprising:

a longitudinal section extending along a first plane;

a lateral section extending from the longitudinal section along a second plane; and a plurality of receptacles extending from the lateral section, each of the receptacles substantially perpendicular to the second plane, each of the receptacles forming a polygon cross-section, each of the receptacles comprising a receptacle aperture configured to receive one of the standoffs;

wherein each of the receptacles forms a plurality of sides, each of the sides comprising a protrusion extending from a first end of the receptacle to a location closer to a second end of the receptacle than the first end of the receptacle, the protrusion configured to prevent the standoff from rotating.

20. An assembly for use in an X-ray generation unit of a medical imaging device, the assembly comprising:

a core assembly comprising:

a magnetic core;

a plurality of insulated cables configured to electrically couple to the magnetic core; and a plurality of standoffs, each of the standoffs configured to couple to an end of each of the insulated cables; and a core mount configured to receive the core assembly, the core mount comprising:

a longitudinal section extending along a first plane, the longitudinal section comprising:

a first planar portion extending along the first plane;

a second planar portion offset from the first plane; and a third planar portion extending along the first plane;

a lateral section extending from the longitudinal section along a second plane; and a plurality of receptacles extending from the lateral section, each of the receptacles comprising a receptacle aperture configured to receive one of the standoffs;

wherein the second planar portion extends between the first planar portion and the third planar portion.

* * * * *